US011672768B2

(12) United States Patent
Zhu et al.

(10) Patent No.: US 11,672,768 B2
(45) Date of Patent: Jun. 13, 2023

(54) SKIN CONTACT ADHESIVE AND METHODS FOR ITS PREPARATION AND USE

(71) Applicant: Dow Silicones Corporation, Midland, MI (US)

(72) Inventors: Bizhong Zhu, Midland, MI (US); Martin Grasmann, Midland, MI (US); Vinita Pandit, Midland, MI (US); David Pierre, Watermael-Boit (BE); Bertrand Louis Julien Lenoble, Silly (BE)

(73) Assignee: DOW SILICONES CORPORATION, Midland, MI (US)

( * ) Notice: Subject to any disclaimer, the term of this patent is extended or adjusted under 35 U.S.C. 154(b) by 1044 days.

(21) Appl. No.: 16/334,546

(22) PCT Filed: Aug. 18, 2017

(86) PCT No.: PCT/US2017/047467
§ 371 (c)(1),
(2) Date: Mar. 19, 2019

(87) PCT Pub. No.: WO2018/052645
PCT Pub. Date: Mar. 22, 2018

(65) Prior Publication Data
US 2021/0283066 A1 Sep. 16, 2021

Related U.S. Application Data

(60) Provisional application No. 62/396,328, filed on Sep. 19, 2016, provisional application No. 62/396,323, filed on Sep. 19, 2016.

(30) Foreign Application Priority Data

Feb. 15, 2017 (EP) .................................. 17305166

(51) Int. Cl.
A61K 9/70 (2006.01)
A61L 15/58 (2006.01)
A61L 24/04 (2006.01)
C08G 18/18 (2006.01)
C08G 18/42 (2006.01)
C08G 18/44 (2006.01)
C08G 18/48 (2006.01)
C08G 18/61 (2006.01)
C08G 18/67 (2006.01)
C08G 18/73 (2006.01)
C08G 18/75 (2006.01)
C08G 18/81 (2006.01)
C09D 175/16 (2006.01)
(Continued)

(52) U.S. Cl.
CPC .......... A61K 9/7069 (2013.01); A61L 15/585 (2013.01); A61L 24/046 (2013.01); C08G 18/18 (2013.01); C08G 18/4283 (2013.01); C08G 18/44 (2013.01); C08G 18/4825 (2013.01); C08G 18/4841 (2013.01); C08G 18/4845 (2013.01); C08G 18/61 (2013.01); C08G 18/6715 (2013.01); C08G 18/73 (2013.01); C08G 18/755 (2013.01); C08G 18/8166 (2013.01); C09D 175/16 (2013.01); C09J 175/16 (2013.01); C09J 183/04 (2013.01)

(58) Field of Classification Search
CPC .................. A61F 13/00; A61F 13/0253; A61F 2013/00655; A61K 8/0208; A61K 8/898; A61K 9/7046; A61K 9/7069; A61K 31/045; A61K 31/167; A61K 31/192; A61K 31/245; A61K 31/405; A61L 15/58; A61L 15/585; A61L 24/04; A61L 24/046; A61Q 1/02; A61Q 5/02; A61Q 5/12; A61Q 19/00; C08G 18/18; C08G 18/246; C08G 18/282; C08G 18/4009; C08G 18/4283; C08G 18/44; C08G 18/4825; C08G 18/4833; C08G 18/4841; C08G 18/4845; C08G 18/61; C08G 18/6715; C08G 18/675; C08G 18/73; C08G 18/755; C08G 18/8166; C08K 5/0025; C08L 75/04; C09J 175/04; C09J 175/16; C09J 183/04
See application file for complete search history.

(56) References Cited

U.S. PATENT DOCUMENTS 3,159,601 A 12/1964 Ashby
3,220,972 A 11/1965 Lamoreaux
(Continued)

FOREIGN PATENT DOCUMENTS

CN 201333128 10/2009
CN 202283306 6/2012
(Continued)

OTHER PUBLICATIONS

Krawczyk, Tobias, "Siloxane modification of polyurethane resins for application in coatings to improve the properties of the film" Master's thesis.
(Continued)

Primary Examiner — Sanza L. McClendon
(74) Attorney, Agent, or Firm — Catherine Brown

(57) ABSTRACT

A crosslinkable composition is useful for preparing a skin contact adhesive or a coating on a substrate. The crosslinkable composition includes (A) a polyurethane-polyorganosiloxane copolymer and (B) a curing catalyst. The skin contact adhesive prepared by crosslinking the crosslinkable composition is useful in applications such as adhesives for medical tapes, adhesives for wound dressings, adhesives for prosthetics, ostomy appliance adhesives, adhesives for medical monitoring appliances, adhesives for scar therapy treatments, adhesives for cosmetic patches, and transdermal drug delivery systems.

19 Claims, 4 Drawing Sheets

(51) Int. Cl.
*C09J 175/16* (2006.01)
*C09J 183/04* (2006.01)

(56) References Cited

U.S. PATENT DOCUMENTS

| | | | |
|---|---|---|---|
| 3,296,291 | A | 1/1967 | Chalk et al. |
| 3,419,593 | A | 12/1968 | Willing |
| 3,516,946 | A | 6/1970 | Modic |
| 3,814,730 | A | 6/1974 | Karstedt |
| 3,989,668 | A | 11/1976 | Lee et al. |
| 4,122,029 | A | 10/1978 | Gee et al. |
| 4,684,538 | A | 8/1987 | Klemarczyk |
| 4,766,176 | A | 8/1988 | Lee et al. |
| 4,784,879 | A | 11/1988 | Lee et al. |
| 4,793,555 | A | 12/1988 | Lee et al. |
| 4,840,796 | A | 6/1989 | Sweet et al. |
| 4,929,669 | A | 5/1990 | Jensen |
| 4,951,657 | A | 8/1990 | Pfister et al. |
| 5,017,654 | A | 5/1991 | Togashi et al. |
| 5,036,117 | A | 7/1991 | Chung et al. |
| 5,075,399 | A | 12/1991 | Ahmed et al. |
| 5,082,886 | A | 1/1992 | Jeram et al. |
| 5,155,149 | A | 10/1992 | Atwater et al. |
| 5,175,325 | A | 12/1992 | Brown et al. |
| 5,258,211 | A | 11/1993 | Momii et al. |
| 5,356,706 | A | 10/1994 | Shores |
| 5,387,417 | A | 2/1995 | Rentsch |
| 5,574,122 | A | 11/1996 | Yeske et al. |
| 5,643,581 | A | 7/1997 | Mougin et al. |
| 5,756,572 | A | 5/1998 | Sweet et al. |
| 5,811,487 | A | 9/1998 | Schulz, Jr. et al. |
| 5,919,441 | A | 7/1999 | Mendolia et al. |
| 5,919,884 | A | 7/1999 | Fink et al. |
| 5,981,680 | A | 11/1999 | Petroff et al. |
| 5,986,018 | A * | 11/1999 | Yamaguchi .......... C09D 175/16 524/379 |
| 5,998,694 | A | 12/1999 | Jensen et al. |
| 6,051,216 | A | 4/2000 | Barr et al. |
| 6,524,564 | B1 | 2/2003 | Kim et al. |
| 6,528,121 | B2 | 3/2003 | Ona et al. |
| 6,623,537 | B1 | 10/2003 | Shores |
| 6,746,765 | B1 | 6/2004 | Fattman |
| 6,750,309 | B1 * | 6/2004 | Chu .................. C09J 175/16 528/25 |
| 6,770,728 | B2 * | 8/2004 | Watanabe .......... C08G 18/8175 528/69 |
| 6,858,218 | B2 | 2/2005 | Lai et al. |
| 6,884,853 | B1 | 4/2005 | Asaoka et al. |
| 6,916,464 | B2 | 7/2005 | Hansenne et al. |
| 7,074,873 | B2 | 7/2006 | Lai et al. |
| 7,423,074 | B2 * | 9/2008 | Lai .................... G02B 1/043 526/321 |
| 7,452,956 | B2 | 11/2008 | Cheng et al. |
| 7,914,160 | B2 | 3/2011 | Sugano |
| 8,377,425 | B2 | 2/2013 | Fleissman et al. |
| 8,507,081 | B2 | 8/2013 | Strobech et al. |
| 8,760,100 | B2 | 6/2014 | Shafer et al. |
| 8,785,587 | B2 | 7/2014 | Wagner et al. |
| 8,877,885 | B2 | 11/2014 | Vyakaranam et al. |
| 9,492,171 | B2 | 11/2016 | Patenaude |
| 9,688,879 | B2 | 6/2017 | Chen et al. |
| 9,976,041 | B2 | 5/2018 | Fu et al. |
| 10,092,441 | B2 | 10/2018 | Lee |
| 10,369,096 | B2 | 8/2019 | Sakamoto et al. |
| 2002/0040202 | A1 | 4/2002 | Levin |
| 2002/0132909 | A1 | 9/2002 | Klanica et al. |
| 2002/0198280 | A1 | 12/2002 | Baba et al. |
| 2003/0072730 | A1 | 4/2003 | Toumilhac |
| 2003/0125500 | A1 * | 7/2003 | Watanabe .......... C08G 18/672 528/54 |
| 2003/0142526 | A1 | 7/2003 | Nakahara et al. |
| 2003/0170188 | A1 | 9/2003 | Ferrari et al. |
| 2003/0235552 | A1 | 12/2003 | Yu |
| 2003/0235553 | A1 | 12/2003 | Lu et al. |
| 2004/0091692 | A1 | 5/2004 | Parrinello et al. |
| 2004/0180032 | A1 | 9/2004 | Manelski et al. |
| 2004/0254325 | A1 | 12/2004 | Keupher et al. |
| 2005/0048104 | A1 | 3/2005 | Venkatraman et al. |
| 2005/0163978 | A1 | 7/2005 | Strobech et al. |
| 2005/0238611 | A1 | 10/2005 | Rando et al. |
| 2006/0036055 | A1 * | 2/2006 | Schafer .............. C08G 77/458 528/44 |
| 2006/0142526 | A1 | 6/2006 | Lai et al. |
| 2006/0247403 | A1 | 11/2006 | Nguyen-Kim et al. |
| 2007/0027285 | A1 | 2/2007 | Gunatillake et al. |
| 2007/0071700 | A1 | 3/2007 | Abhimanyu Patil et al. |
| 2007/0093618 | A1 | 4/2007 | Cheng et al. |
| 2007/0154440 | A1 | 7/2007 | Fleissman et al. |
| 2007/0172518 | A1 | 7/2007 | Raul et al. |
| 2008/0027366 | A1 | 1/2008 | Da Silva Macedo, Jr. |
| 2009/0105670 | A1 | 4/2009 | Bentley et al. |
| 2010/0098648 | A1 | 4/2010 | Yu |
| 2011/0034847 | A1 | 2/2011 | Bougherara |
| 2014/0142490 | A1 | 5/2014 | Johannison |
| 2014/0323941 | A1 | 10/2014 | Lee |
| 2015/0031797 | A1 | 1/2015 | Onodera et al. |
| 2015/0086713 | A1 * | 3/2015 | Chen ................ C08G 18/34 524/839 |
| 2015/0313593 | A1 | 11/2015 | Patenaude |
| 2017/0319463 | A1 | 11/2017 | Sakamoto et al. |
| 2018/0009997 | A1 | 1/2018 | Bhagwagar et al. |
| 2018/0023245 | A1 | 1/2018 | Dams et al. |
| 2020/0002460 | A1 | 1/2020 | Zhu et al. |

FOREIGN PATENT DOCUMENTS

| | | | |
|---|---|---|---|
| CN | 102757705 | 10/2012 | |
| CN | 103937437 | 7/2014 | |
| CN | 201864218 | 12/2015 | |
| DE | 69817234 | 5/2014 | |
| EP | 0347895 | 12/1989 | |
| EP | 1266647 | 12/2002 | |
| EP | 1266648 | 12/2002 | |
| EP | 1266653 | 12/2002 | |
| EP | 3127931 | 8/2017 | |
| WO | 2003105789 | 12/2003 | |
| WO | 2003106614 | 12/2003 | |
| WO | 2004000247 | 12/2003 | |
| WO | 2004054523 | 7/2004 | |
| WO | 2004054524 | 7/2004 | |
| WO | 2004060101 | 7/2004 | |
| WO | 2007092350 | 8/2007 | |
| WO | 2008088491 | 7/2008 | |
| WO | 2013011691 | 1/2013 | |
| WO | 2013030580 | 3/2013 | |
| WO | 2014116281 | 7/2014 | |
| WO | WO-2015031927 A1 * | 3/2015 | ............ C08F 2/50 |
| WO | WO-2015057505 A1 * | 4/2015 | ......... C08G 18/222 |
| WO | 2015075448 | 5/2015 | |
| WO | 2015097064 | 7/2015 | |
| WO | 2015152110 | 10/2015 | |
| WO | 2018052644 | 3/2018 | |
| WO | 2018052647 | 3/2018 | |

OTHER PUBLICATIONS

Search report from corresponding China 201780057529.9 application, dated Oct. 21, 2020.

Huiya Yuan et al., Allyl ether modified light-curing polyurethane acrylate; Applied Chemistry, vol. 20, No. 8; p. 744-748.

Search report from corresponding Japan 22019-513380 application, dated May 11, 2020.

Search report from corresponding Korea 10-2019-7009148 application, dated Nov. 20, 2020.

Balaban, The effect of polar solvents on the synthesis of poly(urethane-urea-siloxane)s, Journal of the Serbian Chemical Society, 2012, p. 1457-1481.

Borde, "Increased water transport in PDMS silicone films by addition of excipients" Acta Biomaterialia 8 (2012) 579-588.

(56) References Cited

OTHER PUBLICATIONS

Chen-Chi, "Intermolecular and Intramolecular Hydrogen Bonding of Poly(dimethylsiloxane)urethane-Graft_Ploy (methylmethacrylate) Copolymers Based on 2,4-TDI and m-XDI" J. App. Polym. Sci., 2002, 962-972.
Chein-Hong, "Novel siliconehydrogel based on PDMS and PEGMA for contact lens application" olloids and Surfaces B: Biointerfaces 123 (2014) 986-994.
Chein-Hong, "Hemocompatibility and cytocompatibility of styrenesulfonate-grafted PDMS-polyurethane-HEMA Hydrogel" Colloids and Surfaces B: Biointerfaces 70 (2009) 132-141.
Ching-Hsien, "Designed drug-release systems having various breathable polyurethane film-backed hydrocolloid acrylated adhesive layers for moisture healing" 2081-2088.
Chung, "Cheracterization and low temperature test of the flexibly crosslinked polyurethane copolymer by poly (dimethylsiloxane)" High Performance Polymenrs, 24(3), 200-209.
Delvalle, Cindy, et al., "Personal Care Applications for Phenylsilsesquioxane Resins," IP.com, 2016, No. IPCOM000248667D.
Dolmaire, "Modification of the Hygrophilic Linear Polyurethane by Crosslinking with a Polydimethylsiloxane. Influence of the Crosslink Density and of the Hydrophobic/Hydrophilic Balance on the Water Transport Properties." Journal of Polymer Science, vol. 44, p. 48-61.
Dzunuzovic, "Investigation of the Morphology and Surface Properties of Crosslinked Poly(Urethane-Ester-Siloxane)s" Hem. Ind. 66 (6) 813-821 (2012). English Summary.
Dzunuzovic, "Synthesis and swelling behavior of polyurethane networks based on hyperbranched polymer" Hem Ind. 65 (6) 637-644(2011).
Ekin. "Combinatorial and High-Throughput Screening of the Effect of Siloxane Composition on the Surface Properties of Crosslinked Siloxane-Polyurethane Coatings" J. Comb. Chem. 2007, 9, 178-188.
Fang, et al., "New formulations capabilities with three new silicone resin flake products", IP.com Prior Art Database Technical Disclosure.
Ferris, et al., "Synthesis of Functional Sugar-Based Polyurethanes" Macromlecular Chemistry and Physics., vol. 213, No. 5, Mar. 16, 2012, pp. 480-488, XP055452383 DE IDDS: 1022-1352, DOI: 10.1002/macp.201100672 abstract.
Garaud, et al., "A Second Generation Silicone Acrylate for US in Beauty Care Applications", IP.com Prior Art Database Technical Disclosure.
Ioan, "Dymanic-machanical and differential scanning calorimetry measurements on crosslinked poly(ester-siloxanes)-urethanes", Polymer 42, 2001, p. 3633-3639.
Jaing, Moisture-Cured Polyurethane/Polysiloxane Copolymers: Effects of the Structure of Polyester Diol and NCO/OH Ratio J. App. Polym. Sci., 2008.
Klode, et al., "Investigation of adhesion of modem wound dressings: a comparative analysis of 56 different wound dressings", Journal of European Academy of Dermatology and Venereology, 2011, 25, pp. 933-939.
Kozakiewicz, "Water-cured poly(urethane-urea)s containing soft segments originating from siloxane/carbonate macrodiols", Polimery, 2012, p. 933-939.
Manriquez, "Evaluation of a New Silicone Adhesive Tape among Clinicians Caring for Patients with Fragile or At-Risk Skin", 2014, p. 163-173, Lippincott Williams & Wilkins.
Mikhailova, "Heat-Resistant and Anti-Corrosion Urethane-Silicone-based Coatings", 2012. p. 197-208.
Oktay, "Polydimethylsiloxane (PDMS)-based antibacterial organic-inorganic hybrid coatings" J. Coat, Technol. Res., 10 (6) 785-798, 2013.
Pergal, "Microstructure and properties of poly(urethane-silicone)s based on hyperbranched polyester of the fourth pseudo generation", Progress in Organic Coatings, 2013, p. 743-756.
Pergal, "Poy(urethane-siloxane)s based on hyperbranched polyester as crosslinking agent: synthesis and characterization", Journal of the Serbian Chemical Society, 2012, p. 919-935.
Pergal, "Study on the morphology and thermomechanical properties of poly(urethane-siloxane) networks based on hyperbranched polyester" Hem. Ind. 67 (6) 871-879 (2013).
Pergal, "Surface and thermomechanical characterization of polyurethane networks based on poly(dimethylsiloxane) and hyperbranched polyester" eXPRESS Polymer Letters vol. 7, No. 10 (2013) 806-820.
Pieper, "Cominatorial approach to study the effect of acrylic polyol composition on the properties of crosslinked siloxane-polyurethane fouling-release coatings" J. Coat. Technol. Res., 4 (4) 453-461, 2007.
Pusztai, "The effect of some disiloxane chain extenders on the thermal and mechanical properties of cross-linked poly (siloxane-urethanes)s" eXPRESS Polymer Letters vol. 7, No. 5 (2013) 456-470.
Souliotis, "A cost and clinical effectiveness analysis among wound healing dressings versus traditional methods in home care patients with pressure ulcers", 2016—p. 596-601.
Yang, "Preparation and Surface Properties of Silicone-Modified Polyester-Based Polyurethane Coats", JCT Research, vol. 3, No. 4, Oct. 2006.
Young-Hee. "Synthesis and Properties of Waterborne Poly(urethaneurea)s Containing Polydiemthylsiloxane" J. App, Polym. Sci., 2010.
Zhu, Synthesis and Thermal Properties of Polyurethane-Polysiloxane Crosslinked Polymer Networks J. App. Poly. Sci., 2003.

\* cited by examiner 100
101
104
102
105
103

Figure 2A
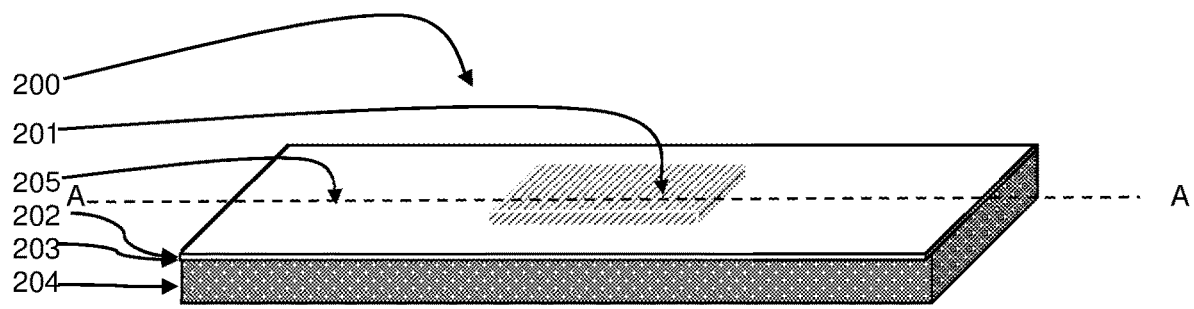
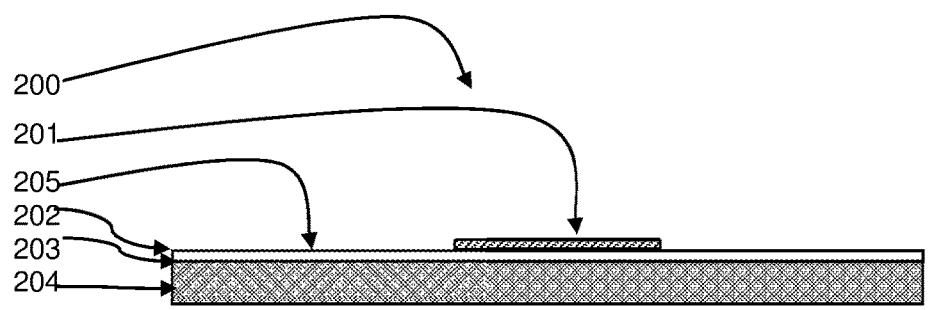
Figure 2B

SKIN CONTACT ADHESIVE AND METHODS FOR ITS PREPARATION AND USE

CROSS REFERENCE TO RELATED APPLICATIONS

This application is a U.S. national stage filing under 35 U.S.C. § 371 of PCT Application No. PCT/US2017/047467 filed on 18 Aug. 2017, currently pending, which claims the benefit of U.S. Provisional Patent Application No. 62/396,328 filed 19 Sep. 2016 under 35 U.S.C. § 119 (e). PCT Application No. PCT/US2017/047467 and U.S. Provisional Patent Application No. 62/396,328 are hereby incorporated by reference.

TECHNICAL FIELD

A crosslinkable composition is useful for preparing a skin contact adhesive composition and a coating composition. The preparation and use of the compositions are disclosed. The compositions include a polyurethane-polyorganosiloxane copolymer.

BACKGROUND

Various types of skin contact adhesives have been proposed for skin contact applications such as adhesives for medical tapes, adhesives for wound dressings, adhesives for prosthetics, ostomy appliance adhesives, adhesives for medical monitoring appliances, adhesives for scar therapy treatments, and transdermal drug delivery systems. Hydrocolloid adhesives and acrylate adhesives typically have the highest adhesion (e.g., require the highest energy to remove from the skin). Polyurethane adhesives have the next highest adhesion, and silicones have the lowest adhesion of these types of skin contact adhesives. Those skin contact adhesives with higher adhesion (requiring higher energy to remove) can cause more pain and potential trauma to the skin during removal than those with lower energy required for removal. Certain skin contact adhesives may also leave an undesirable residue on skin during removal.

In the process of chronic wound care, adhesive wound dressings and/or medical tapes, may cause pain and injury in and around the wound during dressing changes. Repeated application and removal of skin contact adhesives can be painful and traumatic, especially for patients with fragile skin. Fragile skin is generally characterized by thin skin that tears easily and may be more common in older adults than other populations. Aging, sun exposure, and genetics all play a role in thinning of the skin. Certain medications, such as long-term use of oral or topical corticosteroids, can also weaken skin and the blood vessels within the skin and make it more vulnerable to trauma associated with removal of adhesives. Individuals with fragile skin can also experience a loss of cohesion between the epidermis and dermis and between the dermis and subcutaneous tissue, making these individuals more prone to skin tears and trauma, particularly when skin contact adhesives with higher adhesion are used.

Furthermore, silicone adhesives, e.g., those prepared from two part catalyzed silicone elastomers, may be unsuitable for use in certain skin contact adhesive applications, such as transdermal drug delivery. Certain catalysts used to prepare silicone elastomers (such as platinum group metal catalysts for hydrosilylation) may detrimentally affect the medically active ingredient in transdermal drug delivery devices.

In addition to skin contact adhesives, polyurethanes and polyorganosiloxanes are also used for coatings applied on various substrates. Polyurethanes are known to have high mechanical toughness but have limitations such as limited temperature resistance, moisture resistance, and radiation stability. Polyorganosiloxanes are environmentally very stable. Incorporating some polyorganosiloxane into a polyurethane based coating is challenging in the industry because the chemical natures of polyorganosiloxanes and polyurethanes have very limited compatibility.

Problem to be Solved

There is an industry need to develop skin contact adhesives with one or more of the following benefits: good adhesive properties, ability to transfer an active ingredient e.g., in transdermal drug delivery applications, moisture resistance (from the environment to the skin), water transport from the skin to the environment, stability, minimal skin irritation, minimal damage to the skin during use and removal, and/or minimal residue on skin during and after removal. There is also an industrial industry need to develop a composition that can be used to form a coating on a substrate with one or more of the following benefits: improved compatibility between polyurethane and silicones, improved weathering resistance, hydrophobicity, hydrolytic stability, radiation resistance, thermal resistance, corrosion resistance, surface smoothness and gloss, scratch resistance, lower viscosity at similar solid content (impacting volatile organic content, VOC), and reduced friction.

SUMMARY OF THE INVENTION

A crosslinkable composition comprises:
(A) a polyurethane-polyorganosiloxane copolymer, (B) a curing catalyst, and optionally (C) a crosslinker. The polyurethane-polyorganosiloxane copolymer comprises units of formulae:

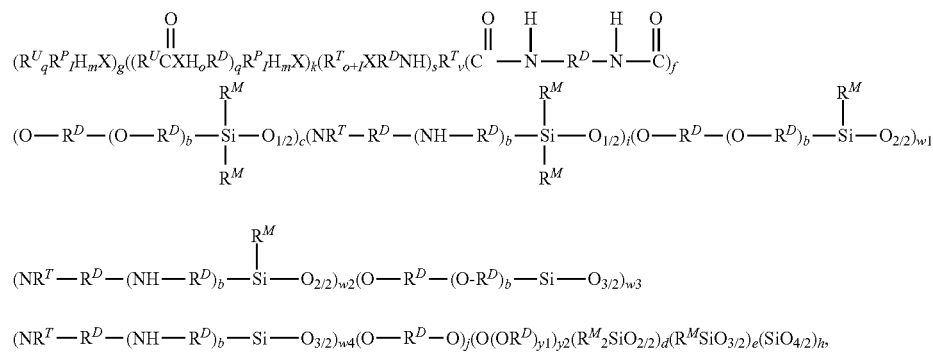

where each $R^U$ is independently a monovalent unsaturated hydrocarbon group; each $R^D$ is independently a divalent hydrocarbon group or a divalent halogenated hydrocarbon group; each $R^M$ is independently a monovalent hydrocarbon group or a monovalent halogenated hydrocarbon group; each $R^P$ is a hydrocarbon group that is divalent, trivalent, or tetravalent or a halogenated hydrocarbon group that is divalent, trivalent, or tetravalent; each $R^T$ is independently hydrogen or a monovalent hydrocarbon group; each subscript b is independently 0 to 1,000,000; subscript c is 0 to 200,000, subscript i is 0 to 200,000, subscript w1 is 0 to 200,000, subscript w2 is 0 to 200,000, subscript w3 is 0 to 200,000, subscript w4 is 0 to 200,000, and a quantity (c+i+w1+w2+w3+w4)≥1; values for each subscripts d, e, and h depend on molecular weight of one of the siloxane segments in the copolymer and are without limit, bound by the molecular weights reachable by the state of the art of the siloxane synthesis chemistry, however, subscript d may be 0 to 1,000,000; subscript e may be 0 to 1,000,000; subscript h may be 0 to 1,000,000, and with the proviso that a quantity (d+e+h)≥1; subscript f is 1 to 1,500,000; subscript g is 0 to 500,000, subscript k is to 500,000, and a quantity (g+k)≥1; subscript j 0; each X is independently nitrogen, oxygen, or sulfur; subscript l=0 or 1 when X is nitrogen, and subscript l=1 when X is oxygen or sulfur; subscript m=1 when X is nitrogen and subscript l=1, and subscript m=0 when X is oxygen or sulfur; subscript o=0 when X is oxygen or sulfur, and subscript o=1 when X is nitrogen; each subscript q independently has a value such that 0≤q≤3; subscript s is 0 to 200,000; subscript v is 0 to 200,000; subscript y1 is 0 to 1,000,000; and subscript y2≥0.

A skin contact adhesive composition comprises starting materials (A) and (B) (and optionally (C)) described above and further comprises one or more of starting materials (D) an active agent, and (E) an excipient. A method for making the skin contact adhesive composition comprises: mixing ingredients comprising (A) the polyurethane-polyorganosiloxane copolymer, and (B) the curing catalyst, and optionally (C) a crosslinker, and one or more of (D) the active agent, and (E) the excipient; thereby preparing a crosslinkable skin contact adhesive composition. A skin contact adhesive may be prepared by a method comprising: exposing the crosslinkable composition described above to heat and/or radiation; thereby forming the skin contact adhesive.

The skin contact adhesive is useful in a laminate article for various skin contact applications such as adhesives for medical tapes, adhesives for wound dressings, adhesives for prosthetics, ostomy appliance adhesives, adhesives for medical monitoring appliances, adhesives for scar therapy treatments, and transdermal drug delivery systems.

A coating composition comprises starting materials (A) and (B) (and optionally (C)) described above and further comprises a coating additive. The coating composition can be applied onto various substrates and can be crosslinked to form a coating on the substrate.

BRIEF DESCRIPTION OF THE DRAWINGS

FIG. 2A shows a perspective view of a wound dressing in the form of an adhesive bandage 200 including the skin contact adhesive 202 described herein.

FIG. 2B shows a cross sectional view of the adhesive bandage 200 taken along line A—A in FIG. 2A.

Figure 1:
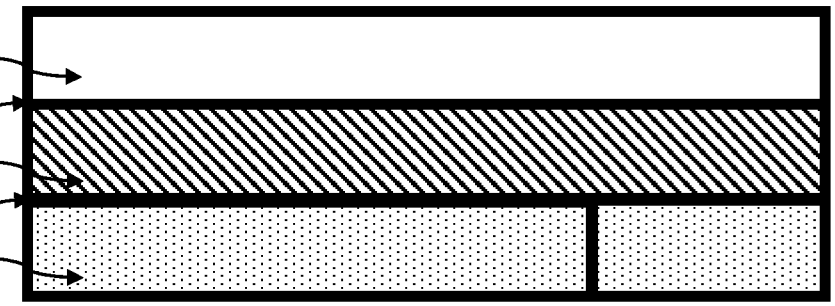
FIG. 1 is a partial cross section of a laminate article 100 including the skin contact adhesive described herein.

REFERENCE NUMERALS 100 laminate article
101 support
102 skin contact adhesive
103 release liner
104 skin facing surface
105 skin contacting surface adhesive
200 adhesive bandage
201 absorbent layer
202 skin contact adhesive
203 skin facing surface
204 support
205 skin contact surface
300 laminate article
301 opposed surface of the carrier
302 carrier
303 opposed surface of the support
304 support
305 skin facing surface of the support
306 absorbent layer
307 opposed surface of the skin contact
308 skin contact adhesive
309 skin facing surface of the skin contact adhesive
310 release liner
400 flange
401 support member
402 skin contact adhesive
403 aperture

DETAILED DESCRIPTION OF THE INVENTION

A crosslinkable composition is useful for preparing a skin contact adhesive. The crosslinkable composition comprises: (A) a polyurethane-polyorganosiloxane copolymer, and (B) a curing catalyst.

(A) Polyurethane-Polyorganosiloxane Copolymer

The polyurethane-polyorganosiloxane copolymer comprises units of formulae:

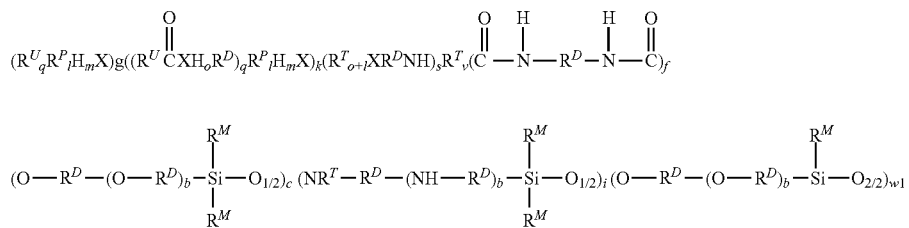

-continued

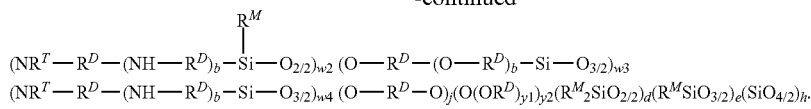
$(NR^T-R^D-(NH-R^D)_b-Si-O_{3/2})_{w4} (O-R^D-O)_j(O(OR^D)_{y1})_{y2}(R^M_2SiO_{2/2})_d(R^MSiO_{3/2})_e(SiO_{4/2})_h.$ In the unit formula above, each $R^U$ is independently a monovalent aliphatically unsaturated hydrocarbon group. Each $R^U$ may have 2 to 13 carbon atoms. Each $R^U$ may be alkenyl or alkynyl, as defined below. Alternatively, each $R^U$ may be independently selected from alkenyl groups such as vinyl, allyl, butenyl, or hexenyl; alternatively vinyl or allyl.

Each $R^D$ is independently a divalent hydrocarbon group or a divalent halogenated hydrocarbon group, as defined below. Each $R^D$ may independently have 2 to 13 carbon atoms. Alternatively, each $R^D$ may be selected from alkylene such as ethylene or propylene, arylene such as phenylene, or alkaralkylene. Alternatively, each $R^D$ may be an alkylene group such as ethylene or propylene.

Each $R^M$ is independently a monovalent hydrocarbon group or a monovalent halogenated hydrocarbon group as defined below. Each $R^M$ may have 1 to 13 carbon atoms. Alternatively, each $R^M$ may be a monovalent hydrocarbon group free of aliphatic unsaturation. For example, each $R^M$ may be independently selected from alkyl such as methyl, ethyl, propyl, butyl or hexyl; aryl such as phenyl, or aralkyl such as tolyl, xylyl or phenyl-methyl. Alternatively, each $R^M$ may be methyl or phenyl, and alternatively each $R^M$ may be methyl.

Each $R^P$ is a divalent, trivalent, or tetravalent hydrocarbon group or a divalent, trivalent or tetravalent halogenated hydrocarbon group. Each $R^P$ may be a divalent, trivalent, or tetravalent hydrocarbon group; alternatively each $R^P$ may be a divalent hydrocarbon group, as described above for each $R^D$.

Each $R^T$ is hydrogen or a monovalent hydrocarbon group. The monovalent hydrocarbon group for $R^T$ may have 1 to 13 carbon atoms. The monovalent hydrocarbon group for $R^T$ is group independently selected from alkyl such as methyl, ethyl, propyl, butyl, or hexyl; aryl such as phenyl; or aralkyl such as tolyl, xylyl, or phenyl-methyl. Alternatively, each $R^T$ may be methyl or phenyl. Alternatively each $R^T$ may be hydrogen or methyl.

Each subscript b is independently greater than or equal to 0. Alternatively, subscript b is 0 to 1,000,000. Alternatively, subscript b is 0 to 200,000. Alternatively, subscript b is 0 to 100,000. Alternatively, subscript b is 0 to 50,000. Alternatively, subscript b is 0 to 10,000. Alternatively, subscript b is 0 to 5,000. Alternatively, subscript b is 0 to 1,000. Alternatively, subscript b is 0 to 500. Alternatively, subscript b is 0 to 100. Alternatively, subscript b is 1 to 100. Alternatively, subscript b is 1 to 50. Alternatively, subscript b is 1 to 20. Alternatively, subscript b is 0 to 1. Alternatively, subscript b=1. Alternatively, subscript b=2. Alternatively, subscript b=3. Alternatively, subscript b=4. Alternatively, subscript b=5.

Subscript c≥0. Alternatively, subscript c is 0 to 200,000. Alternatively, subscript c is 0 to 100,000. Alternatively, subscript c is 0 to 50,000. Alternatively, subscript c is 0 to 10,000. Alternatively, subscript c is 0 to 5,000. Alternatively, subscript c is 0 to 1,000. Alternatively, subscript c is 0 to 500. Alternatively, subscript c is 0 to 100. Alternatively, subscript c is 0 to 50. Alternatively, subscript c is 0 to 20. Alternatively, subscript c is 0 to 10. Alternatively, subscript c is 1 to 100. Alternatively, subscript c is 1 to 50. Alternatively, subscript c is 1 to 20. Alternatively, subscript c is 1 to 10.

Subscript i≥0. Alternatively, subscript i is 0 to 200,000. Alternatively, subscript i is 0 to 100,000. Alternatively, subscript i is 0 to 50,000. Alternatively, subscript i is 0 to 10,000. Alternatively, subscript i is 0 to 5,000. Alternatively, subscript i is 0 to 1,000. Alternatively, subscript i is 0 to 500. Alternatively, subscript i is 0 to 100. Alternatively, subscript i is 0 to 50. Alternatively, subscript i is 0 to 20. Alternatively, subscript i is 0 to 10. Alternatively, subscript i is 1 to 100. Alternatively, subscript i is 1 to 50. Alternatively, subscript i is 1 to 20. Alternatively, subscript i is 1 to 10.

Subscript w1≤0. Alternatively, subscript w1 is 0 to 200,000. Alternatively, subscript w1 is 0 to 50,000. Alternatively, subscript w1 is 0 to 10,000. Alternatively, subscript w1 is 0 to 5,000. Alternatively, subscript w1 is 0 to 1,000. Alternatively, subscript w1 is 0 to 500. Alternatively, subscript w1 is 0 to 100. Alternatively, subscript w1 is 0 to 50. Alternatively, subscript w1 is 0 to 20. Alternatively, subscript w1 is 0 to 10. Alternatively, subscript w1 is 1 to 100. Alternatively, subscript w1 is 1 to 50. Alternatively, subscript w1 is 1 to 20. Alternatively, subscript w1 is 1 to 10.

Subscript w2≥0. Alternatively, subscript w2 is 0 to 200,000. Alternatively, subscript w2 is 0 to 50,000. Alternatively, subscript w2 is 0 to 10,000. Alternatively, subscript w2 is 0 to 5,000. Alternatively, subscript w2 is 0 to 1,000. Alternatively, subscript w2 is 0 to 500. Alternatively, subscript w2 is 0 to 100. Alternatively, subscript w2 is 0 to 50. Alternatively, subscript w2 is 0 to 20. Alternatively, subscript w2 is 0 to 10. Alternatively, subscript w2 is 1 to 100. Alternatively, subscript w2 is 1 to 50. Alternatively, subscript w2 is 1 to 20. Alternatively, subscript w2 is 1 to 10.

Subscript w3≥0. Alternatively, subscript w3 is 0 to 200,000. Alternatively, subscript w3 is 0 to 50,000. Alternatively, subscript w3 is 0 to 10,000. Alternatively, subscript w3 is 0 to 5,000. Alternatively, subscript w3 is 0 to 1,000. Alternatively, subscript w3 is 0 to 500. Alternatively, subscript w3 is 0 to 100. Alternatively, subscript w3 is 0 to 50. Alternatively, subscript w3 is 0 to 20. Alternatively, subscript w3 is 0 to 10. Alternatively, subscript w3 is 1 to 100. Alternatively, subscript w3 is 1 to 50. Alternatively, subscript w3 is 1 to 20. Alternatively, subscript w3 is 1 to 10.

Subscript w4≥0. Alternatively, subscript w4 is 0 To 200,000. Alternatively, subscript w4 is 0 to 50,000. Alternatively, subscript w4 is 0 to 10,000. Alternatively, subscript w4 is 0 to 5,000. Alternatively, subscript w4 is 0 to 1,000. Alternatively, subscript w4 is 0 to 500. Alternatively, subscript w4 is 0 to 100. Alternatively, subscript w4 is 0 to 50. Alternatively, subscript w4 is 0 to 20. Alternatively, subscript w4 is 0 to 10. Alternatively, subscript w4 is 1 to 100. Alternatively, subscript w4 is 1 to 50. Alternatively, subscript w4 is 1 to 20. Alternatively, subscript w4 is 1 to 10.

A quantity (c+i+w1+w2+w3+w4)≥1. Alternatively, in one embodiment i=w2=w4=0, and a quantity (c+w1+w3)≥1, for example, when the polyurethane-polyorganosiloxane copolymer is prepared using a carbinol terminated polyorganosiloxane, as described below. In an alternative embodiment, c=w1=w3=0, and a quantity (i+w1+w3)≥1, for example, when the polyurethane-polyorganosiloxane copolymer is prepared using an amine terminated polyorganosiloxane, as described below.

Each X is independently nitrogen (N), oxygen (O), or sulfur (S). Alternatively, X is N or O. Alternatively, each X is N. Alternatively, each X is O. Subscript m=1 when X is N, and subscript l=1. Subscript m=0 when X is O or S. When X is nitrogen, and subscript l=0; then subscript m is 0. Subscript l is 0 or 1 when X is N, and subscript l=1 when X is O or S. Subscript o=0 when X is O or S, and subscript o=1 when X is N.

Subscript q indicates the number of aliphatically unsaturated hydrocarbon groups at a terminus of the polymer. In the formula above, $0<q\leq3$. Alternatively, $1<q\leq3$, alternatively, $1\leq q\leq3$, and alternatively $2\leq q\leq3$.

Subscripts d, e, and h depend on the molecular weight of one of the siloxane segments in the copolymer and may be without limit (e.g., bound only by the molecular weights reachable by the state of the art of siloxane synthesis chemistry). However, subscript d may be 0 to 1,000,000; subscript e may be 0 to 1,000,000; subscript h may be 0 to 1,000,000, and with the proviso that a quantity $(d+e+h)\geq1$. Subscript $d\geq0$. Alternatively, subscript $d>0$. Alternatively, subscript d is 0 to 200,000, alternatively 0 to 100,000, alternatively 0 to 50,000, alternatively 0 to 10,000, alternatively 0 to 5,000, alternatively 0 to 1,000, alternatively 1 to 1,000, alternatively 1 to 500, and alternatively 1 to 200.

Subscript $e\geq0$. Alternatively, subscript e is 0 to 1,000,000. Alternatively, subscript e is 0 to 200,000, and alternatively 0 to 100,000, alternatively 0 to 50,000, alternatively 0 to 10,000, alternatively 0 to 5,000, alternatively 0 to 1,000, alternatively 1 to 1,000, alternatively 1 to 500, and alternatively 1 to 200. Alternatively, subscript e=0.

Subscript f indicates the number of urethane and/or urea units in the polyurethane-polyorganosiloxane copolymer. Subscript $f\geq1$. Alternatively, subscript f is 1 to 1,500,000. Alternatively, subscript f is 1 to 500,000, and alternatively 1 to 200,000, alternatively 1 to 50,000, alternatively 1 to 10,000, alternatively 1 to 5,000, alternatively 1 to 1,000, alternatively 1 to 500, and alternatively 1 to 200.

Subscript $g\geq0$. Alternatively, subscript g is 0 to 500,000. Alternatively, subscript g is 0 to 200,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200. Subscript $k\geq0$. Alternatively, subscript k is 0 to 500,000. Alternatively, subscript k is 0 to 200,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200. A quantity $(g+k)\geq1$. Alternatively, $1\leq(g+k)\leq1,000,000$. Alternatively $1\leq(g+k)\leq500,000$, alternatively $1\leq(g+k)\leq50,000$, alternatively $1\leq(g+k)\leq10,000$, alternatively $1\leq(g+k)\leq5,000$, alternatively $1\leq(g+k)\leq500$, and alternatively $1\leq(g+k)\leq100$.

Subscript h is $\geq0$. Alternatively, subscript h is 0 to 1,000,000. Alternatively, subscript h is 0 to 200,000, and alternatively 0 to 100,000, alternatively 0 to 50,000, alternatively 0 to 10,000, alternatively 0 to 5,000, alternatively 0 to 1,000, alternatively 1 to 1,000, alternatively 1 to 500, and alternatively 1 to 200. Alternatively, subscript h=0.

Subscript j is $\geq0$. Alternatively, subscript j is 0 to 500,000. Alternatively, subscript j is 0 to 200,000, and alternatively 0 to 100,000, alternatively 0 to 50,000, alternatively 1 to 10,000, alternatively 1 to 5,000, alternatively 1 to 1,000, alternatively 1 to 500, and alternatively 1 to 200. Subscript j is >0 when a chain extender is used in making the copolymer.

Subscript s is $\geq0$. Alternatively, subscript s is 0 to 200,000. Alternatively, subscript s is 0 to 150,000, and alternatively 0 to 100,000, alternatively 0 to 50,000, alternatively 1 to 10,000, alternatively 1 to 5,000, alternatively 1 to 1,000, alternatively 1 to 500, and alternatively 1 to 200.

Subscript v is $\geq0$. Alternatively, subscript v is 0 to 200,000. Alternatively, subscript v is 0 to 150,000, and alternatively 0 to 100,000, alternatively 0 to 50,000, alternatively 1 to 10,000, alternatively 1 to 5,000, alternatively 1 to 1,000, alternatively 1 to 500, and alternatively 1 to 200.

Each subscript y1 is independently greater than or equal to 0. Alternatively, subscript y1 is 0 to 1,000,000. Alternatively, subscript y1 is 0 to 200,000. Alternatively, subscript y1 is 0 to 100,000. Alternatively, subscript y1 is 0 to 50,000. Alternatively, subscript y1 is 0 to 10,000. Alternatively, subscript y1 is 0 to 5,000. Alternatively, subscript y1 is 0 to 1,000. Alternatively, subscript y1 is 0 to 500. Alternatively, subscript y1 is 0 to 100. Alternatively, subscript y1 is 1 to 100. Alternatively, subscript y1 is 1 to 50. Alternatively, subscript y1 is 1 to 20. Alternatively, subscript y1 is 0 to 1. Alternatively, subscript y1=0. Alternatively, subscript y1=1. Alternatively, subscript y1=2. Alternatively, subscript y1=3. Alternatively, subscript y1=4. Alternatively, subscript y1=5.

Subscript y2 is $\geq0$. Alternatively, subscript y2 is 0 to 500,000. Alternatively, subscript y2 is 0 to 200,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200. Subscript y2 is >0 when a chain extender is used in making the copolymer.

Alternatively, when subscripts $l=m=k=s=v=l=j=w1=w2=w3=w4=e=h=0$, the copolymer may have formula (I):

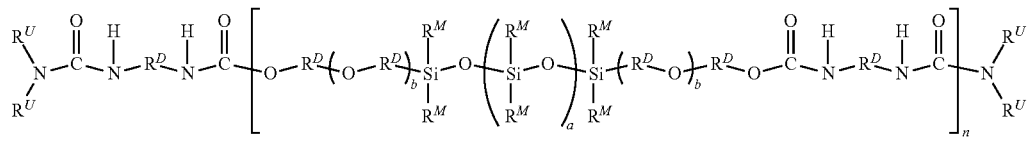

where $R^U$, $R^D$, and $R^M$ are as described above, each subscript a is independently 0 to 1,000,000, each subscript b is independently greater than or equal to 0, and subscript n is greater than or equal to 1. Alternatively, subscript a is 0 to 200,000, alternatively 0 to 100,000, alternatively 0 to 50,000, alternatively 0 to 10,000, alternatively 0 to 5,000, alternatively 0 to 1,000, alternatively 1 to 1,000, alternatively 1 to 500, alternatively 1 to 200, and alternatively 5 to 150. Subscript n is 1 to 1,500,000. Alternatively, subscript n is 1 to 500,000, and alternatively 1 to 200,000, alternatively 1 to 50,000, alternatively 1 to 10,000, alternatively 1 to 5,000, alternatively 1 to 1,000, alternatively 1 to 500, and alternatively 1 to 200. Each subscript $b\geq0$. Alternatively, subscript b is 0 to 1,000,000. Alternatively, subscript b is 0 to 200,000. Alternatively, subscript b is 0 to 100,000. Alternatively, subscript b is 0 to 50,000. Alternatively, subscript b is 0 to 10,000. Alternatively, subscript b is 0 to 5,000. Alternatively, subscript b is 0 to 1,000. Alternatively, subscript b is 0 to 500. Alternatively, subscript b is 0 to 100. Alternatively, subscript b is 1 to 100. Alternatively, subscript b is 1 to 50. Alternatively, subscript b is 1 to 20. Alternatively, subscript b is 0 to 1. Alternatively, subscript b=0. Alternatively, subscript b=1. Alternatively, subscript b=2. Alternatively, subscript b=3. Alternatively, subscript b=4. Alternatively, subscript b=5.

Alternatively, the copolymer may have formula (II):

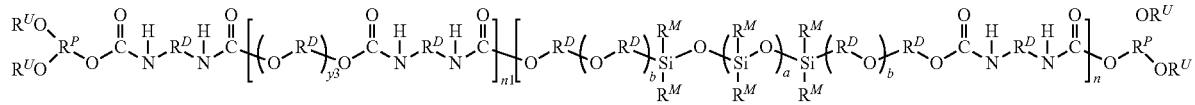

where $R^U$, $R^D$, subscript a, subscript b, subscript n are as described above for formula (I), each subscript y3 is 1 to 200,000, and subscript n1 is 1 to 1,500,000. Alternatively, subscript y3 is 1 to 100,000. Alternatively, subscript y3 is 1 to 50,000. Alternatively, subscript y3 is 1 to 10,000. Alternatively, subscript y3 is 1 to 5,000. Alternatively, subscript y3 is 1 to 1,000. Alternatively, subscript y3 is 1 to 500. Alternatively, subscript y3 is 1 to 100. Alternatively, subscript y3 is 1 to 100. Alternatively, subscript y3 is 1 to 50. Alternatively, subscript y3 is 1 to 20. Alternatively, subscript y3=2. Alternatively, subscript y3=5. Alternatively, subscript y3=9. Alternatively, subscript y3=20. Alternatively, subscript y3=40. Alternatively, subscript n1 is 1 to 500,000. Alternatively, subscript n1 is 1 to 200,000. Alternatively, subscript n1 is 1 to 50,000. Alternatively, subscript n1 is 1 to 10,000. Alternatively, subscript n1 is 1 to 5,000. Alternatively, subscript n1 is 1 to 1,000. Alternatively, subscript n1 is 1 to 500. Alternatively, subscript n1 is 1 to 200.

Method for Making the Copolymer.

The polyurethane-polyorganosiloxane copolymer described above may be prepared by a method comprising:
i) reacting starting materials comprising:
   a) an isocyanate compound, and
   b) a polyorganosiloxane, thereby preparing a polyurethane-polyorganosiloxane prepolymer; and
ii) reacting the prepolymer prepared in step i) with a starting material comprising c) an endblocker having an average of one or more aliphatically unsaturated group per molecule; thereby preparing the polyurethane-polyorganosiloxane copolymer.

Alternatively, in a second embodiment, the polyurethane-polyorganosiloxane copolymer may be prepared by a method comprising:
i) reacting starting materials comprising:
   a) an isocyanate compound, and
   c) an endblocker having an average of one or more aliphatically unsaturated group per molecule, thereby preparing a urethane functional intermediate; and
ii) reacting the polyurethane functional intermediate prepared in step i) with a starting material comprising b) a polyorganosiloxane; thereby preparing the polyurethane-polyorganosiloxane copolymer.

In each embodiment of the method described above, b) the polyorganosiloxane may be b1) a carbinol terminated polyorganosiloxane, b2) an amine terminated polyorganosiloxane, or a mixture of both b1) and b2).

Alternatively, in each embodiment of the method described above, d) a chain extender may optionally be added as a starting material in addition to a) the isocyanate, b) the polyorganosiloxane, and c) the endblocker. Starting material d), the chain extender, may be added before, during, and/or after step i) in each embodiment of the method described above. In one embodiment, b) the polyorganosiloxane may be pre-reacted with d) the chain extender before reacting b) the polyorganosiloxane in the method. Alternatively, a) the isocyanate compound may be pre-reacted with d) the chain extender before reacting the a) isocyanate compound in the method.

Starting Material a) Isocyanate Compound

In the method described above, a) the isocyanate compound has an average of one or more isocyanate groups per molecule. Alternatively, the isocyanate compound may have an average of two or more isocyanate groups per molecule. The isocyanate compound may have formula: $R-(N=C=O)_p$, where R is a polyvalent hydrocarbon group or a polyvalent halogenated hydrocarbon group and subscript p is an integer representing the number of isocyanate groups per molecule. Subscript p is greater than or equal to 1. Alternatively subscript p is 2, 3, or 4; alternatively subscript p is 2 or 3; and alternatively, subscript p is 2. R is a divalent hydrocarbon group when subscript p is 2. R is a trivalent hydrocarbon group when subscript p is 3. R is a tetravalent hydrocarbon group when subscript p is 4.

The isocyanate compound is exemplified by monomeric isocyanates and polymeric isocyanates. Monomeric isocyanates include aromatic diisocyanates such as meta-tetramethyl xylene diisocyanate (TMXDI), toluene diisocyanate (TDI), phenylene diisocyanate, xylene diisocyanate, 1,5-naphthalene diisocyanate, chlorophenylene 2,4-diisocyanate, bitoluene diisocyanate, dianisidine diisocyanate, toluidine diisocyanate and alkylated benzene diisocyanates; aliphatic and cycloaliphatic isocyanates such as hexamethylene diisocyanate (HDI), hydrogenated methylene diphenyl diisocyanate (HMDI), 1-isocyanato-3-isocyanatomethyl-3,5,5-trimethyl-cyclohexane (isophorone diisocyanate, IPDI), and nonanetriisocyanate (TTI), methylene-interrupted aromatic diisocyanates such as methylene-diphenyl-diisocyanate, especially the 4,4'-isomer (MDI) including alkylated analogs such as 3,3'-dimethyl-4,4'-diphenyl-methane diisocyanate; hydrogenated materials such as cyclohexylene diisocyanate, 4,4'-methylenedicyclohexyl diisocyanate; mixed aralkyl diisocyanates such as the tetramethylxylyl diisocyanates, 1,4-bis(1-isocyanato-1,1'-dimethylmethyl) benzene, and polymethylene isocyanates such as 1,4-tetramethylene diisocyanate, 1,5-pentamethylene diisocyanate, 1,6-hexamethylene diisocyanate (HDI), 1,7-heptamethylene diisocyanate, 2,2,4- and 2,4,4-trimethylhexamethylene diisocyanate, 1,10-decamethylene diisocyanate, and 2-methyl-1,5-pentamethylene diisocyanate; vinylisocyanate; and combinations thereof.

Polymeric isocyanates include dimerized isocyanates uretdiones, uretidinediones and carbodiimide, trimerized isocyanates, isocyanurates, iminooxadiazine dione, uretonimine, and linear polymer α-Nylon; and derivatized isocyanates by reacting difunctional or multifunctional isocyanates with various compounds to form allophanate, or biuret compounds, or isocyanate functional urethane or other prepolymers. Some of the polyisocyanates are difunctional, i.e., having 2 isocyanate groups per molecule. Some have more than two isocyanate groups. An example is polymeric diphenylmethane diisocyanate, which is a mixture of molecules with two-, three-, and four- or more isocyanate groups, which may have an average functionality greater than two, commonly 2.7. Isocyanate functional compounds with isocyanate functionality greater than two may act as crosslinking sites. Commercially available isocyanate functional organic compounds are illustrated by Tolonate XIDT 70SB, an isophorone diisocyanate trimer (70% solids, 12.3 wt % NCO) sold by Rhodia (Cranbury, N.J.) and Desmodur N-100 polyisocyanate (available from Mobay Corp.).

Alternatively, a) the isocyanate compound may comprise a blocked isocyanate. The isocyanate group can be blocked by common blocking agents such as phenol, nonyl phenol, butanone oxime, caprolactam, and others. These blocked isocyanates can be released by any conventional means such as heating at a temperature above room temperature to react with chain extenders and polyorganosiloxanes to construct the polyurethane-polyorganosiloxane copolymer.

Starting Material b1) Carbinol-Functional Polyorganosiloxane

In the method described above, b1) the carbinol-functional polyorganosiloxane comprises units of formulae:

200,000, alternatively 0 to 200,000, alternatively 0 to 100,000, alternatively 0 to 50,000, alternatively 0 to 10,000, alternatively 0 to 5,000, alternatively 0 to 1,000, alternatively 1 to 1,000, alternatively 1 to 500, alternatively 1 to 200, and alternatively 5 to 150. Alternatively, each $R^{DX}$ is O.

Starting Material b2) Amine-Functional Polyorganosiloxane

The amine functional polyorganosiloxane comprises units of formulae:

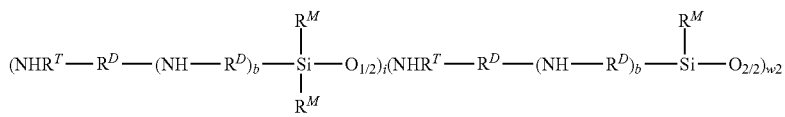

$(NHR^T—R^D—(NH—R^D)_b—Si—O_{3/2})_{w4}(R^M{}_2SiO)_d(R^M\text{-}SiO_{3/2})_e(SiO_{4/2})_h$, and subscripts b, d, e, h, and i are as described above.

An exemplary amine terminated polyorganosiloxane comprises a terminal unit of formula

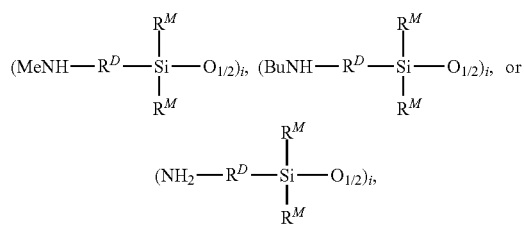

where Me represents a methyl group and Bu represents a butyl group; and further comprises one or more of

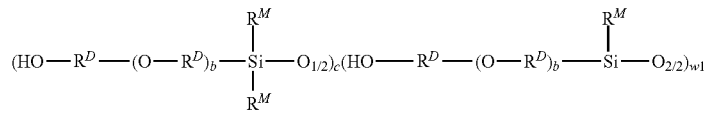

$(HO—R^D—(O—R^D)_b—Si—O_{3/2})_{w3}(R^M{}_2SiO)_d(R^MSiO_{3/2})_e(SiO_{4/2})_h$. In this unit formula, each $R^M$, $R^D$, subscript b, subscript c, subscript w1, subscript w3, subscript d, subscript e, and subscript h are as described above. Examples of carbinol-functional polyorganosiloxanes are disclosed in WO2008/088491, U.S. Pat. Nos. 6,528,121, and 7,452,956. The carbinol groups may be at terminal positions, pendent positions, or both terminal and pendent positions in the carbinol-functional polyorganosiloxane. Alternatively, the carbinol groups may be at terminal positions.

Alternatively, b1) the carbinol-functional polyorganosiloxane may comprise an α,ω-difunctional polydiorganosiloxane of formula (II): $R^CR^M{}_2Si—R^{DX}—(R^M{}_2SiO)_rR^{DX}—SiR^M{}_2R^C$, where, each $R^C$ is independently a carbinol functional group of formula $HO—R^D—(OR^D)_b—$ where subscript b, $R^M$ and $R^D$ are as described above, each $R^{DX}$ is independently selected from 0 or a divalent hydrocarbon group described above as $R^D$, and subscript r represents the degree of polymerization of the carbinol-terminated polyorganosiloxane of formula (II). Subscript r>0. Alternatively, subscript r may be 1 to 1,000,000, alternatively 50 to 1,000, and alternatively 200 to 700. Alternatively, subscript r is 0 to $(R^M{}_2SiO_{2/2})_d(R^MSiO_{3/2})_e(SiO_{4/2})_h$, where $R^M$, $R^D$, and subscripts l, d, e, and h are as described above.

Starting Material c) Endblocker

The endblocker is a compound having an average of more than one aliphatically unsaturated group per molecule, and said compound is selected from an amine compound, an alcohol, or a thiol compound. The endblocker may be selected from compounds of formulae: (III)

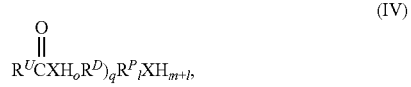

or mixtures of compounds (III) and (IV), where $R^U$, $R^P$, $R^D$, and X and subscripts q, l, m, and o are as described above. The endblocker is added in an amount sufficient to provide a molar ratio of endblocker to isocyante (XH/N=C=O)<1.

Alternatively, the endblocker may be an amine compound. The amine compound may have formula $R^U{}_zN(R^D)_{2-z}H$, where $R^U$ is as described above, and subscript z>0, alternatively 0<z≤2, and alternatively z=2. Examples of suitable amine compounds for the endblocker include diethyl amine and diallyl amine.

Starting Material d) Chain Extender

The chain extender may be a dialcohol, of formula HO—$R^D$—OH, where $R^D$ is as defined above. Suitable dialcohols include 1,3-butanediol; 1,4-butanediol; 1,6-hexanediol, 1,10-decanediol; 1,6-hexamethylenediol; 2,2-dimethyl-1,3-propanediol; 1,4-cyclohexanedimethylol; 1,1'-isopropylidine-bis-(p-phenylene-oxy)-di-2-ethanol; poly (tetrmethylene ether) glycol; and ethylene glycol. Alternatively, the chain extender may be a diamine containing 2 to 20 carbon atoms e.g., 1,2-diaminoethane; 1,4-diaminobutane; 1,2-propanediamine; hexamethylenediamine; diethylene diamine; 5-amino-1-(aminomethyl)-1,3,3-trimethylcyclohexane; 4,4'-methylene bis (cyclohexylamine); and ethanol amine. Alternatively, the chain extender may be a dithiol, a dicarboxylic acid, or a diepoxide. Suitable chain extenders are disclosed, for example, in U.S. Pat. Nos. 4,840,796 and 5,756,572.

Starting Material e) Optional Additional Enblocker.

After the reaction step ii) as described above, optionally the reaction product can be treated with an additional end blocker. This additional end blocker, e), can be such that it leaves an additional reactive group on the copolymer after end blocking reaction, or it leaves an unreactive group on the copolymer after the end blocking reaction. Suitable such end blockers for starting material e) include but are not limited to alcohols such ethanol, propanol, butanol, carboxylic acids such as acetic acid, and alcohols and carboxylic acids containing aliphatic unsaturation. Thio-alcohols, hydroxylamines, glycol, amino acids, and amino sugars are also suitable as additional endblocking agents. When isocyanate is present in molar excess during preparation of the copolymer, unreacted isocyanate can be present in the copolymer. Starting material e), the additional endblocker may be added to react with this residual isocyanate.

Starting Material f) Solvent

A solvent may be added during the method to prepare the polyurethane-polyorganosiloxane copolymer described herein. Any organic compound that will dissolve the polyurethane-polyorganosiloxane copolymer and that is relatively unreactive towards isocyanate, and amine and/or carbinol compounds is suitable as a solvent. Examples include aliphatic hydrocarbons, aromatic hydrocarbons, esters, ethers, ketones, and amides. Exemplary solvents include ethyl acetate, butyl acetate, methyl ethyl ketone, or tetrahydrofuran.

The amount of solvent to be used depends on the properties of the polyurethane-polyorganosiloxane copolymer including structure, molecular weight, and the particular method of copolymer preparation, and can be 0 to 99%. Generally for higher molecular weight copolymers especially when a high torque mixing mechanim will not be used, solvent may be added to reduce the viscosity and make the system easier to handle during performance of the method to make the polyurethane-polyorganosiloxane copolymer. If the molecular weight is relatively low and/or high torque mixing equipment such as a twin screw extruder is used, no solvent needs to be used. When solvent is used, the amount may be 0 to 99%, alternatively 0 to 80%, alternatively 1% to 60%, and alternatively 5% to 50%, based on the combined weights of all starting materials used.

Starting Material q) Catalyst

Reacting b) the polyorganosiloxane with either the isocyanate compound or the isocyanate functional urea intermediate may be catalyzed by starting material g) a catalyst. Suitable catalysts include tertiary amines and metal salts, such as the salts of tin. Tin compounds are useful as catalysts herein include those where the oxidation state of the tin is either +4 or +2, i.e., tin (IV) compounds or tin (II) compounds. Examples of tin (IV) compounds include stannic salts such as dibutyl tin dilaurate, dimethyl tin dilaurate, di-(n-butyl)tin bis-ketonate, dibutyl tin diacetate, dibutyl tin maleate, dibutyl tin diacetylacetonate, dibutyl tin dimethoxide, carbomethoxyphenyl tin tris-uberate, dibutyl tin dioctanoate, dibutyl tin diformate, isobutyl tin triceroate, dimethyl tin dibutyrate, dimethyl tin di-neodecanoate, dibutyl tin di-neodecanoate, triethyl tin tartrate, dibutyl tin dibenzoate, butyltintri-2-ethylhexanoate, dioctyl tin diacetate, tin octylate, tin oleate, tin butyrate, tin naphthenate, dimethyl tin dichloride, a combination thereof, and/or a partial hydrolysis product thereof. Tin (IV) compounds are known in the art and are commercially available, such as Metatin® 740 and Fascat® 4202 from Acima Specialty Chemicals of Switzerland, Europe, which is a business unit of The Dow Chemical Company. Examples of tin (II) compounds include tin (II) salts of organic carboxylic acids such as tin (II) diacetate, tin (II) dioctanoate, tin (II) diethylhexanoate, tin (II) dilaurate, stannous salts of carboxylic acids such as stannous octoate, stannous oleate, stannous acetate, stannous laurate, stannous stearate, stannous naphthanate, stannous hexanoate, stannous succinate, stannous caprylate, and a combination thereof. Other metal salts are also suitable catalysts for this reaction. Examples include zinc salts such as zinc acetate and zinc naphthenate. Salts of lead, bismuth, cobalt, iron, antimony, sodium, such as lead octoate, bismuth nitrate, and sodium acetate can also catalyze this reaction. In certain occasions organomercuric compounds can also be used. Optionally co-catalysts can also be used along with a primary catalyst. And a combination of two or more catalysts can be used, e.g., to provide either faster reaction than achievable with a single catalyst, or a better balanced reaction initiation time and finish time.

Starting Material h) Organic Diol

Starting material (C) is an organic polyol. Suitable organic polyols are organic polymers containing two or more hydroxyl groups. The organic polyol for starting material (C) may be a polyether polyol, a polyester polyol, a polyacrylate polyol, a polycaprolactone polyol, a polyurethane polyol, a polycarbonate polyol, polybutadiene diol, other polymer polyols, or two or more of these organic polyols. Copolymer polyols of two or more types of polymers can also be used. Polyols with other modifications on the polymer structures, such as fluorination, can also be used. Suitable organic polyols alternatively may be an organic polymer diol. Such organic polymer diols include polyalkylene oxide diols e.g., polyethylene oxide diols, polypropylene oxide diols, and polybutylene oxide diols; or polycarbonate diols. Suitable organic polyols alternatively may be small molecule organic diols. Such small molecule organic diols include glycerol. The organic polyol may be added to tune the surface energy and/or hydrophilicity/mechanical properties of the copolymer composition. The amount added may be 0 to 95%, alternatively 0 to 75%, alternatively 0 to 50%, and alternatively 1 to 25%.

The amounts of starting materials a), b), c), and when present one or more of, d), e), f), g), and h), can vary widely, according to the polyorganosiloxane structure and molecular weight desired, to arrive at the polyurethane-polyorganosiloxane copolymer described by the formula herein. The molar ratio of isocyanate groups of starting material a) to the active hydrogen of carbinol or amine groups on the polysiloxane selected for starting material b) can be 0.1 to 100, alternatively 0.1 to 50, alternatively 0.1 to 10, alternatively 0.1 to 2, alternatively 0.1 to 1.5, alternatively 0.1 to 1.25, alternatively 0.1 to 1.1, alternatively 0.1 to 1.05, alternatively 0.1 to 1.01, alternatively 0.1 to 1, alternatively 0.1 to 0.9, alternatively 0.1 to 0.5, alternatively 0.5 to 50, alternatively 0.5 to 10, alternatively 0.5 to 2, alternatively 0.5 to 1.5, alternatively 0.5 to 1.25, alternatively 0.5 to 1.1, alternatively 0.5 to 1.05, alternatively 0.5 to 1.01, alternatively 0.5 to 1, alternatively 0.5 to 0.9, and alternatively 0.4 to 0.7. When this ratio is <1, the reaction is controlled so that the endblocker is added before all the isocyanate groups are consumed. When this ratio is >1, the endblocker can be added before or after all the active hydrogen on the carbinol or amine groups have been reacted. The molar ratio between the endblocker to the isocyanate can be from 0.001 to 0.99, alternatively 0.001 to 0.8, alternatively 0.01 to 0.8, alternatively 0.01 to 0.6, alternatively 0.01 to 0.5, alternatively 0.01 to 0.4, alternatively 0.01 to 0.3, alternatively 0.01 to 0.2, alternatively 0.01 to 0.1, alternatively 0.05 to 0.8, alternatively 0.05 to 0.6, alternatively 0.05 to 0.5, alternatively 0.05 to 0.4, alternatively 0.05 to 0.3, alternatively 0.05 to 0.2, alternatively 0.05 to 0.1. The molar ratio between the isocyante groups to the active hydrogen on the hydroxyl or amine groups or other reactive groups on the chain extender can be 1.001 to 1,000,000, alternatively 1.001 to 500,000, alternatively 1.001 to 200,000, alternatively 1.001 to 100,000, alternatively 1.001 to 50,000, alternatively 1.001 to 10,000, alternatively 1.001 to 5,000, alternatively 1.001 to 1,000, alternatively 1.001 to 500, alternatively 1.001 to 100, alternatively 1.001 to 50, alternatively 1.001 to 20, alternatively 1.001 to 10, alternatively 1.001 to 5, alternatively 1.001 to 4, alternatively 1.001 to 3, alternatively 1.001 to 2, alternatively 1.001 to 1.5, alternatively 1.001 to 1.3, alternatively 1.001 to 1.2, alternatively 1.01 to 20, alternatively 1.01 to 10, alternatively 1.01 to 5, alternatively 1.01 to 4, alternatively 1.01 to 3, alternatively 1.01 to 2, alternatively 1.01 to 1.5, alternatively 1.01 to 1.3, and alternatively 1.01 to 1.2.

Method Conditions

Steps i) and ii) in each embodiment of the method described above may be performed with or without heating. The temperature for the reaction depends on the selection of starting materials a), b), and c) and whether any of d), e), f), g), and/or h) is present, however, the temperature may range from −20° C. to 150° C.; alternatively 0° C. to 100° C., and alternatively 20° C. to 60° C. at pressure of 1 atmosphere. Pressure under which the method is performed is not critical.

Each embodiment of the method described above may be performed in batch, semi-batch, semi-continuous, or continuous mode in any convenient equipment. When preparing higher molecular weight copolymers (e.g., when higher molecular weight starting materials are used), the method may be performed in an extruder, such as a twin screw extruder.

Crosslinkable Composition

The polyurethane-polyorganosiloxane copolymer prepared as described above can be crosslinked by any means that will initiate the reaction of the aliphatic unsaturation. The reaction can be initiated by thermally generated free radicals. It is also ultraviolet radiation crosslinkable via several different means. The aliphatic unsaturation can react with themselves, or additional reactive compounds (crosslinkers) can be added to react with the unsaturation. Suitable crosslinkers include but are not limited to other aliphatically unsaturated compounds such as acrylates and methacrylates, dialkenyl (such as divinyl and diallyl) compounds, thiol (SH containing) compounds, phosphines (PH containing), boranes (BH containing), and silanes (SiH containing). In a first embodiment, a crosslinkable composition comprises: (A) the polyurethane-polyorganosiloxane copolymer described above, and (B) a curing catalyst.

(B) Curing Catalyst

The curing catalyst may be (B1) a free radical initiator or (B2) a hydrosilylation catalyst. The free radical initiator can be a peroxide, which can be thermally activated or activated by a reducing agent at room temperature. The peroxide may have formula $R^{MS}$—O—O—$R^{MS}$, where each $R^{MS}$ is independently a saturated monovalent hydrocarbon group such as alkyl as defined below or saturated monovalent halogenated hydrocarbon group, such as haloalkyl as defined below. Examples of peroxides include di-tert-butyl peroxide, bis(tert-butylperoxy)hexane, dicumyl peroxide, and bis(tert-butylperoxyisopropyl)benzene, 1,1-bis(tert-butyl peroxy)-3,3,3-trimethylcyclohexane, 2,5-dimethyl-2,5-di(tert-butylperoxy)hexane, 2,5-dimethyl-2,5-bis(tert-butylperoxy) hexyne-3, (tert-butylperoxy)myristylcarbonate; and mixtures of two or more thereof. Alternatively, the free radical initiator can be a photo-activated compound. Photo-activated initiators are known in the literature and any known initiating systems can be used. These can be one component systems or two component systems. One component systems include benzoyl-chromophore based systems, substituted benzoyl-chromophore based ones, hydroxyl alkyl heterocyclic ketones, hydroxyl alkyl conjugated ketones, benzophenone- and thioxanthone-moiety-based systems, benzoyl phosphine oxide derivatives, phosphine oxide derivatives, trichloromethyl triazines, biradical generating ketones, some peroxides and diketones, azides and aromatic bis-azides, some azo, disulfide, disilane, diselenide, diphenylditelluride, digermane, and distanane derivatives, and compounds with carbon-germanium, carbon-silicon, carbon-sulfur, sulfur-silicon, sulfur-sulfur, and germanium-silicon cleavable bonds. Two component systems include ketone-hydrogen donor based systems and dye-based systems. Examples of such free radical initiators are known in the art and are commercially available, such as 2-hydroxy-2-methyl-1-phenyl-propan-1-one (commercially available as Darocur 1173). Other commercially available examples include 1-hydroxy-cyclohexyl-phenyl-ketone, benzophenone, 2-hydroxy-1-[4-(2-hydroxyethoxy) phenyl]-2-methyl-1-propanone, methylbenzoylformate, oxy-phenyl-acetic acid 2-[2 oxo-2 phenyl-acetoxy-ethoxy]-ethyl ester, oxy-phenyl-acetic 2-[2-hydroxy-ethoxy]-ethyl ester, alpha-dimethoxy-alpha-phenylacetophenone, 2-benzyl-2-(dimethylamino)-1-[4-(4-morpholinyl) phenyl]-1-butanone, 2-Methyl-1-[4-(methylthio)phenyl]-2-(4-morpholinyl)-1-propanone, diphenyl (2,4,6-trimethylbenzoyl)-phosphine oxide, phenyl bis (2,4,6-trimethyl benzoyl) phosphine oxide, and bis (eta 5-2,4-cyclopentadien-1-yl) or bis [2,6-difluoro-3-(1H-pyrrol-1-yl) phenyl]titanium. The amount of free radical initiator added to this crosslinkable composition depends on various factors including the other ingredients of the composition, however, the amount may range from 0.01% to 10% based on the combined weights of all ingredients added to the composition. Alternatively the amount of free radical initiator may be 0.01% to 5%, alternatively 0.05% to 5%, alternatively 0.05% to 3%, alternatively 0.1% to 10%, alternatively 0.1% to 5%, and alternatively 0.1% to 3%. The composition may be crosslinked by exposure to ultra violet radiation, visible light, or infrared radiation, depending on where sufficient absorption occurs and how the absorbed energy is transferred to activate the initiator and produce free radicals. Alternatively the initiation systems can be activated by heat, or the activation is assisted by heat in combination with electromagnetic radiation. When crosslinking is activated by heat, additionally many other heat activated free radical initiators can be used. Examples include peroxides and azo compounds. Exemplary peroxides are known in the art, for example, those recited in U.S. Pat. Nos. 4,929,669; 5,082,886; 5,258,211; and 5,919,884.

The crosslinkable composition can also be crosslinked by reacting the aliphatic unsaturation with a compound with silicon hydride groups through a hydrosilylation reaction. This reaction is usually catalyzed by metal salts and other compounds, amines and other organic bases, peroxides, and/or complexes, and organic peroxides can be used to catalyze hydrosilylation. Hydrosilylation catalysts are known in the art and are commercially available. Such conventional hydrosilylation catalysts can be a metal selected from platinum, rhodium, ruthenium, palladium, osmium, and iridium. Alternatively, the hydrosilylation catalyst may be a compound of such a metal, for example, chloroplatinic acid, chloroplatinic acid hexahydrate, platinum dichloride, and complexes of said compounds with low molecular weight organopolysiloxanes or platinum compounds microencapsulated in a matrix or core/shell type structure. Complexes of platinum with low molecular weight organopolysiloxanes include 1,3-diethenyl-1,1,3,3-tetramethyldisiloxane complexes with platinum. These complexes may be microencapsulated in a resin matrix. Exemplary hydrosilylation catalysts are described in U.S. Pat. Nos. 3,159,601; 3,220,972; 3,296,291; 3,419,593; 3,516,946; 3,814,730; 3,989,668; 4,784,879; 5,036,117; and 5,175,325 and EP 0 347 895 B. Microencapsulated hydrosilylation catalysts and methods of preparing them are known in the art, as exemplified in U.S. Pat. Nos. 4,766,176 and 5,017,654.

(C) Crosslinker

The crosslinkable composition may optionally further comprise (C) a crosslinker, in addition to starting materials (A) and (B), described above. The crosslinker may be (C1) an acrylate crosslinker, (C2) a crosslinker containing alkenyl groups (other than in an acrylate group), (C3) a thiol-functional crosslinker, or (C4) an SiH containing crosslinker. The acrylate crosslinker and the crosslinker containing other alkenyl groups can contain one or more acrylate or alkenyl (e.g., vinyl) groups per molecule. Examples include but are not limited to methylmethacrylate, n-butyl acrylate, 2-ethyl hexyl methacrylate, ethylene glycol diacrylate, poly(ethylene glycol) diacrylate, neopentyl glycol diacrylate, trimethylolpropane triacrylate, pentaerythritol triacrylate, glycerol propoxylate triacrylate, trimethylolpropane propoxylate triacrylate, trimethylolpropane ethoxylate triacrylate, pentaerythritol tetraacrylate, di(trimethylolpropane) tetraacrylate, divinylbenzene, divinyl sulfone, 1,4-butanediol divinyl ether, ethylene glycol divinyl ether, di-tri-, and poly-ethylene glycol divinyl ether, and styrene.

Thiol-functional crosslinkers suitable for starting material (C3) are known in the art and are commercially available. They can be organic thiol compounds (SH containing compounds) with an average of two or more SH groups per molecule, or mercaptofunctional silanes, siloxanes, polysilanes, polysiloxanes, organosilanes, organosiloxanes, and organopolysiloxanes containing an average of two or more SH groups per molecule. Suitable thiol-functional crosslinkers include: a trimethylsiloxy terminated dimethylsiloxane-methylmercaptopropylsiloxane copolymer with a SH content of 0.35 mol/100 g; a trimethylsiloxy terminated dimethylsiloxane-methylmercaptopropylsiloxane copolymer with a SH content of 0.16 mol/100 g, purchased from Gelest, Inc.; a trimethylsiloxy terminated dimethylsiloxane-methylmercaptopropylsiloxane copolymer with a SH content of 0.05 mol/100 g, purchased from Gelest, Inc.; and a trimethylsiloxy terminated dimethylsiloxane-methylmercaptopropylsiloxane copolymer with a SH content of 0.16 mol/100 g.

The SiH containing crosslinkers suitable for starting material (C4) are also known in the literature and commercially available. These generally include silanes, siloxanes, polysilanes, polysiloxanes, organosilanes, organosiloxanes, and organopolysiloxanes containing an average of two or more silicon bonded hydrogen (SiH) groups per molecule. Examples include phenylmethylsilane, tetramethyldisilane, phenylsilane, γ,ω-dihydrido-polydimethylsiloxane, poly(dimethyl-methylhydrido)siloxane, hydrogenpolysilsesquioxane, poly(methylhydridosiloxane-co-silphenylene), poly(methylhydridosiloxane-co-silmethylene), and other copolymers of M, and/or D, and/or T, and optionally Q siloxane units which have at least 1 hydride (H) bonded to silicon in the M, and/or D, and/or T units, where M stands for the unit of $R^T_3SiO_{1/2}$, D for $R^T_2SiO_{2/2}$, T for $R^TSiO_{3/2}$, and Q for $SiO_{4/2}$, and $R^T$ is as defined above. When the SiH crosslinker is present, the crosslinkable composition may be crosslinked via hydrosilylation reaction, and the crosslinkable composition further comprises a hydrosilylation catalyst, as described above. In this embodiment, a skin contact adhesive prepared using the crosslinkable composition could be used in an application other than a transdermal drug delivery application, or in an application where the hydrosilylation catalyst does not detrimentally affect any active ingredient selected as ingredient (D).

The amount of crosslinker added to the composition depends on various factors including the selection of starting material (A), the selection of starting material (B), the selection of the crosslinker (C) and whether any other starting materials are present in the crosslinkable composition, however, (C) the crosslinker can be added in an amount of 0 to 80%, alternatively 0 to 50%, alternatively 0 to 30%, alternatively 0.5 to 50%, alternatively 0.5 to 30%, alternatively 1% to 50%, alternatively 1% to 30%, alternatively 1% to 20%, alternatively 1% to 10%, alternatively 5% to 50%, alternatively 5% to 30%, and alternatively 5% to 25%, based on the weight of the crosslinkable composition.

This invention further relates to a skin contact adhesive composition. The skin contact adhesive composition comprises starting materials (A), (B) and optionally (C) as described above. The skin contact adhesive further comprises one or both of (D) an active ingredient and (E) an excipient.

(D) Active Ingredient

Ingredient (D) may be added, for example, when the skin contact adhesive composition will be used to prepare a skin contact adhesive in a scar treatment application, a cosmetic patch application, a transdermal drug delivery application, and/or in an application for delivery of the active ingredient to the skin. The specific active ingredients used are not critical to this invention and as used herein the term "active ingredient" is to be construed in its broadest sense as a material intended to produce some beneficial effect on the organism to which it is applied.

Exemplary active ingredients suitable for ingredient (D) include, without limitation, drugs that act upon the central nervous system, drugs affecting renal function, drugs affecting cardiovascular function, drugs affecting gastrointestinal function, drugs for treatment of helminthiasis, antimicrobial agents such as silver, silver compounds, and/or chlorhexidine, nutrients, hormones, steroids, and drugs for treatment of dermatoses; see for example, those disclosed in U.S.

Patent Application Publication US2007/0172518 paragraph [0014] and those listed in PCT Publication WO2007/092350 at pp. 21-28.

Other suitable active ingredients for ingredient (D) include non-steroidal anti-inflammatory drugs such as salicylates e.g., acetylsalicylic acid; propionic acid derivatives e.g., (RS)-2-(4-(2-methylpropyl)phenyl)propanoic acid (ibuprofen); acetic acid derivatives e.g., 2-{1-[(4-chlorophenyl)carbonyl]-5-methoxy-2-methyl-1H-indol-3-yl}acetic acid (indomethacin), enolic acid derivatives; anthranilic acid derivatives, COX-2 inhibitors e.g., N-(4-hydroxyphenyl)ethanamide N-(4-hydroxyphenyl)acetamide (acetaminophen), and sulfonanilides. Other suitable active ingredients for ingredient (D) include local anesthetics such those containing an ester group e.g., ethyl 4-aminobenzoate (benzocaine); those containing an amide group e.g., 2-(diethylamino)-N-(2,6-dimethylphenyl)acetamide (lidocaine); and naturally derived local anesthetics e.g., (1R,2S,5R)-2-isopropyl-5-methylcyclohexanol (menthol).

One skilled in the art would recognize that in the laminate articles described below, (D) the active ingredient may be included in the skin contact adhesive prepared by including ingredient (D) in the skin contact adhesive composition described herein (i.e., before crosslinking said composition to form the skin contact adhesive). Alternatively, (D) the active ingredient may be included in a separate reservoir within the laminate article, and not mixed into the skin contact adhesive prepared from the skin contact adhesive composition.

The amount of (D) the active ingredient used in the skin contact adhesive composition depends on various factors including the type of active ingredient selected for ingredient (D), the and type of laminate article in which the active ingredient will be incorporated, and the selection of any other ingredients in the crosslinkable composition. However, the amount of ingredient (D) may be 0 to 45%, alternatively greater than 0 to 25%, alternatively greater than 0 to 15%, alternatively greater than 0 to 10%, alternatively greater than 0.1% to 10%, alternatively greater than 1% to 10%, based on the weight of the skin contact adhesive composition.

(E) Excipient

The excipient may be any ingredient that is distinct from ingredient (D) that is added to the crosslinkable composition to provide one or more benefits during and/or after making the crosslinkable composition and/or to provide one or more benefits to the skin contact adhesive. For example, the excipient may be (F) a stabilizer, (G) a binder, (H) a filler, (I) a solubilizer, (J) a skin penetration enhancer (e.g., for transdermal drug delivery applications), (K) an adhesion promoter, (L) an agent to improve moisture permeability, or a combination of two or more of (F), (G), (H), (I), (J), (K), and (L).

(F) Stabilizer

The composition may optionally further comprise (F) a stabilizer. The stabilizer may comprise an antioxidant, such as vitamin A, vitamin E, vitamin C, retinyl palmitate, selenium, benzenepropanoic acid, 3,5-bis(1,1dimethylethyl)-4-hycroxy-C7-C9 branched alkyl esters (Irganox® 1135 from BASF), pentaerythritoltetrakis[3-(3,5-di-tert-butyl-4-hydroxyphenyl) propionate] (Irganox® 1010 from BASF), octadecyl-3-(3,5-di-tert-butyl-4-hydroxyphenyl) propionate (Irganox® 1076 from BASF), 1,3,5-Trimethyl-2,4,6-tris(3,5-di-tert-butyl-4-hydroxybenzyl)benzene (Irganox® 1330 also from BASF), 2-methyl-4,6-bis [(octylthio)methyl]phenol (Irganox® 1520 from BASF) 2,6-di-tert-butyl-methylphenol (BHT), 2,2'-methylene-bis-(6-tert-butyl-4-methylphenol) (Vulkanox BKF from LanXess), or mixtures thereof. Alternatively, the stabilizer may comprise an amino acid such as cysteine, methionine, or combinations thereof. Alternatively, the stabilizer may comprise a paraben, such as methyl paraben, propyl paraben, or combinations thereof. The amount of stabilizer depends on various factors including whether the composition will be heated and whether ingredient (D) will be added, however, the stabilizer may be present in an amount from 0 to 2%, alternatively 0 to 1%, alternatively 0.1% to 1%, alternatively 0.2% to 0.7%, and alternatively 0.2% to 0.6% based on the weight of the crosslinkable composition.

(G) Binder

Ingredient (G), a binder, may optionally be added to the crosslinkable composition. Suitable binders include saccharides and their derivatives (e.g., disaccharides such as sucrose and lactose, polysaccharides such as starches or cellulose, or sugar alcohols such as xylitol, sorbitol or malitol. Other suitable binders include proteins such as gelatin. The amount of binder depends on various factors including the type of laminate article and the selection of other ingredients in the composition, however, the amount of binder may be 0 to 50% based on the weight of the crosslinkable composition.

(H) Filler

Ingredient (H), a filler, may optionally be added to the crosslinkable composition. Suitable fillers for ingredient (H) include but are not limited to silica to help prevent cold flow of the crosslinkable composition off the support. The filler selected is of a type and is present in an amount so as not to detrimentally impact adhesion of the skin contact adhesive. The amount of filler may be 0 to 2%, alternatively 0 to 1%, based on the weight of the crosslinkable composition.

(I) Solubilizer

Ingredient (I), a solubilizer, may optionally be added to the crosslinkable composition. Suitable solubilizers include dimethylsulfoxide, povidone (PVP) and natural oils such as mineral oil, sunflower oil, and peanut oil. Esters, glycols, polyether, may help solubilize (D) the active ingredient (i.e., keep ingredient (D) in a noncrystalline state in the crosslinkable composition, and the skin contact adhesive prepared therefrom, to facilitate permeation of the active ingredient to the skin (and/or into the skin). The solubilizer may be present at 0 to 50%, alternatively 0 to 40%, alternatively 0 to 25%, alternatively greater than 0 to 20%, and alternatively 20% to 25%, based on the weight of the crosslinkable composition. Alternatively, the solubilizer suitable for ingredient (I) may be the solvent, described above for making the polyurethane-polyorganosiloxane copolymer.

(J) Skin Penetration Enhancer

Ingredient (J), a skin penetration enhancer, may optionally be added to the crosslinkable composition. Suitable skin penetration enhancers include glycols such as propylene glycol and polyethylene glycol; organic acids such as oleic acid; fatty alcohols such as oleyl alcohol; and amines. The amount of ingredient (J) depends on various factors including where the skin contact adhesive prepared from the crosslinkable composition will be applied, the length of time the skin contact adhesive will be applied, and the purpose (e.g., wound dressing or transdermal drug delivery), however the amount may range from 0 to less than 20%, alternatively 1% to 2% based on the weight of the crosslinkable composition.

(K) Adhesion Promoter

Materials known in the art as skin contact adhesives may be mixed with the composition described herein to adjust adhesive properties, such as release force required to remove the skin contact adhesive and amount of residue remaining on skin. These materials may be used herein as adhesion promoters. Exemplary adhesion promoters include hydrocolloids. The amount of adhesion promoter depends on the type of adhesion promoter selected and the amount of adhesion desired, however the amount of adhesion promoter may be 0 to less than 20%, alternatively 1% to 2%, based on the weight of the crosslinkable composition.

(L) Agent to Improve Moisture Permeability

Ingredient (L) is an agent to improve moisture permeability, which may optionally be added to the crosslinkable composition. Suitable agents for ingredient (L) included but are not limited to hydrocolloids, gelatins, polymers such as CMC carboxymethylcellulose, and polyethylene oxide. The amount of ingredient (L) depends on various factors including the selection of the other ingredients in the crosslinkable composition and the end use for the skin contact adhesive prepared therefrom. However, the amount of ingredient (L), when present, may be 0 to 50%%, alternatively 0.1% to 25%, alternatively 0.1% to 10%, alternatively 1% to 10%, based on the weight of the crosslinkable composition. One skilled in the art would recognize that certain agents that improve moisture permeability may also act as mucoadhesives that make the dressing adhere better as moisture content increases.

When selecting ingredients for the crosslinkable composition described above, there may be overlap between types of ingredients because certain ingredients described herein may have more than one function. For example, certain hydrocolloids may be useful as agents to improve moisture permeability (L) and as adhesion promoters (K). Gelatin may be useful as an agent to improve moisture permeability (L) and as a binder (G). Certain nutrients such as vitamin A and vitamin E may be useful as an active ingredient (D) and a stabilizer (F). When adding ingredients to the crosslinkable composition, the ingredients are distinct from one another.

Skin Contact Adhesive

The skin contact adhesive is prepared by crosslinking the crosslinkable composition described above. Crosslinking may be performed by any convenient means, such as exposing the crosslinkable composition to heat and/or radiation such as electron beam or ultra violet (UV) radiation. When heat is used to crosslink the crosslinkable composition, a temperature from 25 to 200° C. can be used for a duration of less than five seconds to two hours. When electron beam is used to crosslink the crosslinkable composition, an accelerating voltage of 75 kV to 350 kV can be used and a dosage of 5 to 250 kilogray (kGy) is usually sufficient to crosslink the composition. When UV is used, a light source of 200 nm to 450 nm is suitable, and can be generated by a mercury vapor lamp (Type H, D, or V for different wavelengths), a fluorescent lamp, or an UV LED lamp. The power rating of the lamp needed depends on the composition and can be any emitting irradiation at a dosage of at least 0.001 mJ/cm$^2$, alternatively from 0.01 to 2000 mJ/cm$^2$, alternatively from 0.1 to 1000 mJ/cm$^2$, alternatively from 1 to 1000 mJ/cm$^2$, alternatively from 10 to 500 mJ/cm$^2$. Without wishing to be bound by theory, it is thought that the crosslinking reaction will not detrimentally affect ingredient (D), when present.

The skin contact adhesive prepared by crosslinking the crosslinkable composition is useful in applications such as adhesives for medical tapes, adhesives for wound dressings, adhesives for prosthetics, ostomy appliance adhesives, adhesives for medical monitoring appliances, adhesives for cosmetic patches, adhesives for scar therapy treatments, and transdermal drug delivery systems.

Laminate Article

A laminate article comprises:
i) a support having a skin facing surface and an opposed surface, which is intended to be facing away from skin,
ii) a skin contact adhesive on at least a portion of the skin facing surface, where the skin contact adhesive has a skin contact surface opposite the skin facing surface of the support.

The support is a material that can readily be applied to a part of the wearer's body. The support may be a plastic film, such as polyurethane, a polyolefin such as low density polyethylene (LDPE), medium density polyethylene (MDPE), high density polyethylene (HDPE), or polypropylene; a polyolefin/polyurethane composite; polyester; or ethylene vinyl acetate (EVA). Alternatively, the support may be paper, fabric (woven or nonwoven), silicone rubber, or foam. All, or a portion, of the support may optionally have a plurality of holes, e.g., be perforated or apertured, to provide for air permeability in the laminate article. Suitable supports are known, see for example PCT Publications WO2013/030580 and WO2014/116281 at pages 5-6.

The skin contact adhesive is on at least a portion of the skin facing surface of the support. For certain applications, such as transdermal drug delivery, the skin contact adhesive may cover all or most of the skin facing surface of the support to maximize the surface area through which the drug can be transferred. Alternatively, the skin contact adhesive may be on a portion of the skin facing surface of the support, for example, when the skin contact adhesive will be used to adhere an absorbent material to a wound. The amount (thickness) of the skin contact adhesive on the support will vary depending on various factors including the application (e.g., ostomy, wound care, and other applications where strong adhesion for longer time periods may have a thicker skin contact adhesive on the support, but adhesives for transdermal drug delivery or bandages or medical tapes may have a thinner skin contact adhesive on the support. Thickness may be uniform. Alternatively, thickness may be non-uniform on any given support, e.g., thicker toward the middle and thinner at or near the edge of the support). However, thickness of the skin contact adhesive may range from 0.0635 mm to 2.54 mm, alternatively 0.254 mm to 1 mm.

FIG. 1 is a partial cross section of a laminate article 100 according to this invention. The laminate article 100 comprises a support 101 having a layer of skin contact adhesive 102 on a skin facing surface 104 of the support 101. A release liner 103 covers the skin contacting surface 105 of the layer of skin contact adhesive 102. The support 101 may be a backing for a medical tape or adhesive bandage or other wound dressing, and is as described above.

Figure 4:
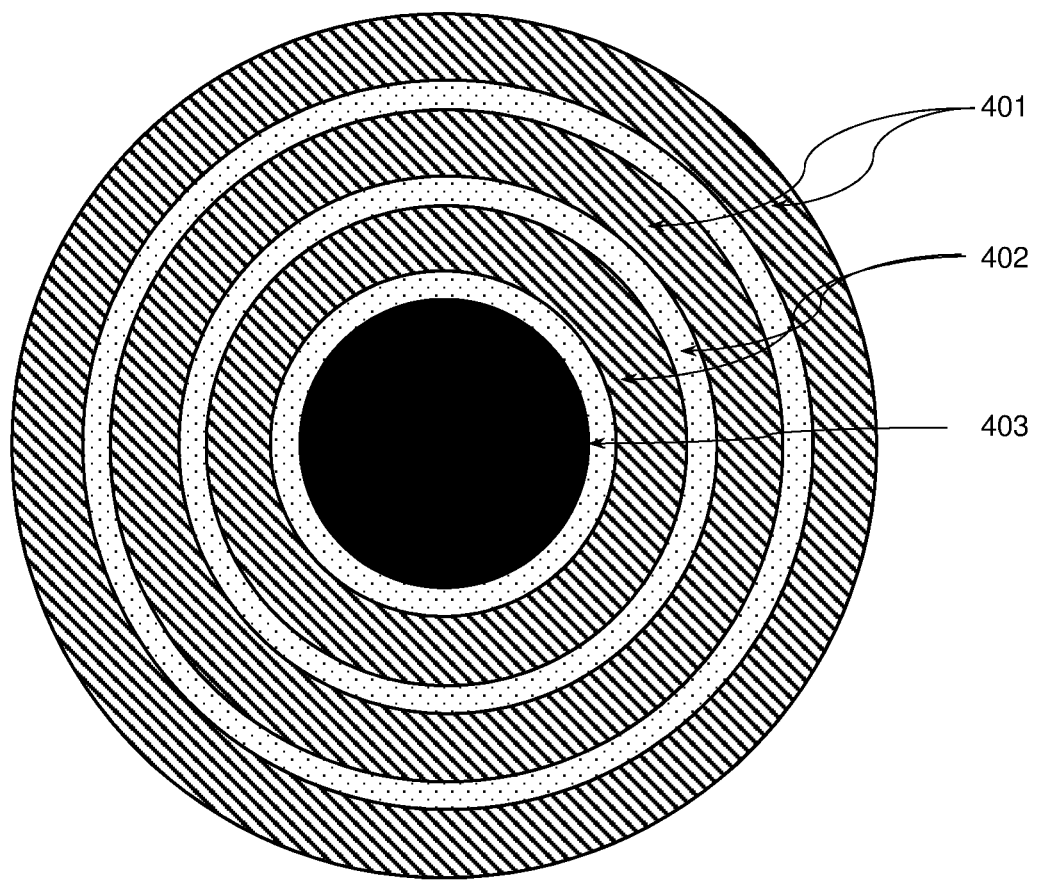
FIG. 4 shows a flange 400 for use in an ostomy appliance including the skin contact adhesive 402 described herein.

The layer of skin contact adhesive can be continuous or discontinuous. When discontinuous, the layer may be in various forms such as lines, line segments, dots, or flecks. The discontinuous forms may be in a uniform pattern across the surface of the support, or have different patterns at different regions of the support. An example is in FIG. 4, which shows a flange 400 for use in an ostomy appliance (not shown). The flange 400 has a support member 401 defining an aperture 403. The skin contact adhesive 402 described herein is formed in a discontinuous layer (shown as circular lines) on the support member 401.

The laminate article may further comprise one or more additional layers. For example, the laminate article may further comprise iii) a release liner covering the skin contact surface of the skin contact adhesive. The release liner is removable and may be used during shipping and storage of the laminate article before use. The skin contact adhesive can be exposed by removal of the release liner.

Suitable release liners include liners made of or coated with polyethylene, polypropylene, fluorocarbons, and fluorosilicone coated release papers and fluorosilicone coated plastic films. Suitable release liners are known and are described for example, in PCT Publication WO2007/092350. Without wishing to be bound by theory, it is thought that one benefit of the skin contact adhesive prepared by crosslinking the crosslinkable composition described herein is that release liners without fluorinated coatings (e.g., without fluorocarbons and without fluorosilicones) can be effectively used with the skin contact adhesive. Release liners with fluorinated coatings are typically more expensive than release liners without a fluorinated coating. Alternatively, release liners include liners made of or coated with polyethylene or polypropylene.

The laminate article may optionally further comprise iv) an absorbent layer. The absorbent layer may be mounted to the skin contact surface of the skin contact adhesive when the absorbent layer will contact the skin (e.g., a wound) directly, such as when the laminate article is an adhesive bandage such as that shown in FIG. 2 or in Canadian Patent Publication CA02585933. FIG. 2A shows a perspective view of an adhesive bandage 200 including a thin layer of the skin contact adhesive 202 described herein. FIG. 2B shows a cross sectional view of the adhesive bandage 200 taken along line A-A in FIG. 2A. The adhesive bandage 200 has a perforated plastic support 204 with the layer of the skin contact adhesive 202 on a skin facing surface 203 of the support 204. An absorbent layer 201 is on the skin contact surface 205 of the skin contact adhesive 202. Alternatively, the absorbent layer may be located between the skin contact adhesive and the support, for example, when the skin contact adhesive described herein is used in a wound dressing such as that shown in PCT Publication WO2007/092350.

The absorbent layer may be any suitable material such as a textile or polymer composition that is capable of absorbing fluid (e.g., exudate from a wound). The absorbent layer may be a commercially available product, see PCT Publication WO2007/092350 for examples of absorbent polymers, at pages 12 to 15. Examples include but are not limited to: thermoplastic polymers, block copolymers (other than ingredient (A)), polyolefins, hydrogels, and hydrocolloids.

The laminate article may further comprise v) a carrier. The carrier may be used to provide some rigidity to the laminate article and to enable the laminate article to be placed over a wound with minimal wrinkling and to avoid having the skin contact adhesive stick to itself during application of the laminate article to a wearer. The carrier may optionally be removed, e.g., after the laminate article is adhesively secured to the skin. The carrier may be mounted on the opposed surface of the support, intended to be facing away from the skin.

The carrier can be ethylene vinyl acetate (EVA), polyethylene film, polyester film, or paper coated with an EVA coating. One skilled in the art would recognize that the carrier may have the same materials of construction as the support, or different materials of construction. The carrier, as used herein, refers to a separate, discrete, piece of the laminate article.

Figure 3:
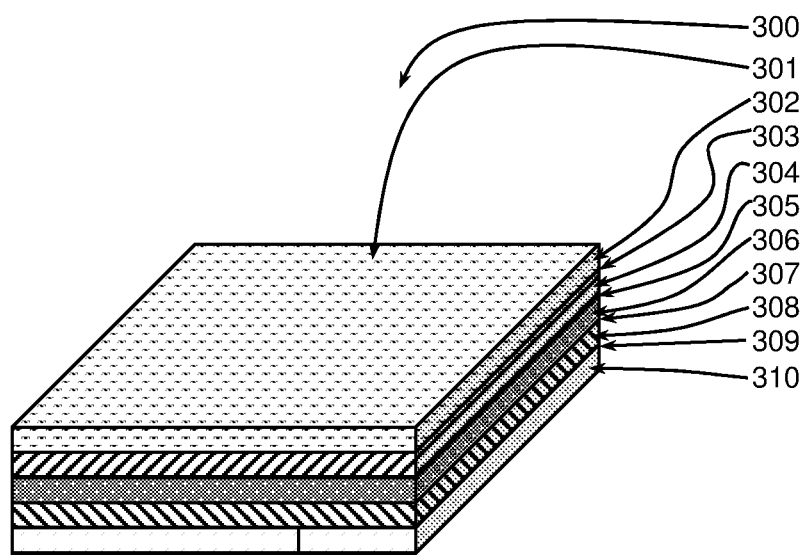
FIG. 3 is a partial cross section of a wound dressing in the form of a laminate article 300 including the skin contact adhesive 308 described herein.

FIG. 3 is a partial cross section of an alternative laminate article 300 according to this invention. The laminate article 300 has a support 304 with a skin facing surface 305 and an opposed surface 303 intended to face away from the skin. The skin contact adhesive (described herein) 308 is mounted to the skin facing surface 305 of the support 304. The skin contact adhesive 308 forms a layer with a skin contact surface 309. A release liner 310 (with two parts that can be peeled away separately) covers the skin contact surface 309 of the skin contact adhesive 308. The laminate article further comprises an absorbent layer 306 between the skin facing surface 305 of the support 304 and the opposed surface 307 of the skin contact adhesive 308. The laminate article further comprises a carrier 302 having a skin facing surface and an opposed surface 301. The carrier 302 is removably affixed to the opposed surface 303 of the support 304.

Method for Making a Laminate Article

A method for making the laminate article comprises:
I) forming a layer of the crosslinkable composition described above on at least a portion of a skin facing surface of a support, and
II) crosslinking the crosslinkable composition to form the skin contact adhesive.

The method may optionally further comprise: III) applying a release liner to a skin contact surface of the skin contact adhesive opposite the skin facing surface of the support. Step III) may be performed either before or after step II). The method may further comprise: IV) compressing the crosslinkable composition between the support and the release liner before crosslinking in step II).

The crosslinkable composition may be applied to support by any convenient means, e.g., dip coating, extrusion, spray coating, knife coating or roll coating. The crosslinkable composition may be applied to the support or the release liner first. The composition may be applied to the support using the method described, for example, in U.S. Patent Application Publication US2007/0172518 (substituting the crosslinkable composition described herein for the matrix described in the reference). Alternatively, the crosslinkable composition may be sandwiched between the support and release liners, and pressure may be applied to form the laminate article and/or crosslink the crosslinkable composition to form the skin contact adhesive. Laminate articles may be prepared as described in WO2015/075448, except using the composition of this invention instead of the polyurethane gel adhesive formulation disclosed in the reference.

The method for making the laminate article may optionally further comprise: III) sterilizing the laminate article. The laminate article including the skin contact adhesive is capable of being sterilized. The laminate article may be sterilized using known sterilizing means such as irradiating (e.g., with electron beam or gamma radiation) and/or heating such as with dry heat or steam. Sterilizing in step III) may be performed as a separate step after step 1) or step II), as described above. Alternatively, sterilizing may be performed concurrently with steps I) and/or step II). For example, heating and/or irradiating may be performed to crosslink the crosslinkable composition, remove solvent, and/or sterilize.

Applications

The skin contact adhesive described herein is suitable for use in various applications. The skin contact adhesive prepared by crosslinking the crosslinkable composition is useful in applications such as adhesives for medical tapes, adhesives for wound dressings, adhesives for prosthetics, ostomy appliance adhesives, adhesives for medical monitoring appliances, adhesives for scar therapy treatments, and transdermal drug delivery systems.

For example, the laminate article described above may comprise the support and the skin contact adhesive described above, on all or a portion of a surface of the support. The skin contact adhesive may be formed in a layer which is continuous or discontinuous. In one embodiment, the laminate article described above may be useful as an adhesive element. The skin contact adhesive may be applied to a skin facing surface of a support, and the skin contact adhesive may be used to adhere the support to the skin of a wearer. For example, the skin contact adhesive described above may be used to adhere a prosthetic to a wearer with a limb difference, or the skin contact adhesive may be used to adhere an ostomy appliance to a patient with a stoma. An ostomy appliance typically comprises a pouch for collection of waste, which is attached to a flange defining an aperture. The flange has an adhesive on the skin facing surface, where the adhesive surrounds the opening for attachment to the skin of a patient with a stoma (as described above in FIG. 4).

The skin contact adhesive described herein may be used in would care and ostomy care applications for adhesion to the skin, instead of the pressure sensitive adhesive disclosed in U.S. Patent Application Publication US2005/0163978, or instead of the adhesive used in U.S. Patent Application Publication US2014/0323941.

The skin contact adhesive described herein is suitable for use in wound dressings. For example, the skin contact adhesive described herein may be used as the skin contacting barrier layer instead of the hydrocolloids in U.S. Pat. No. 5,998,694. The skin contact adhesive described herein may be used in the wound cover of PCT Publication WO2007/092350 and US Patent Application Publications US2009/0105670 and US2015/0313593.

Alternatively, the skin contact adhesive described herein may be used in a transdermal drug delivery system. In this embodiment, the crosslinkable composition described above comprises ingredient (D) the active ingredient and may further comprise (E) the excipient. Without wishing to be bound by theory, it is thought that this invention may provide the benefit that crosslinking the composition to form the skin contact adhesive does not detrimentally affect (D) the active ingredient. The skin contact adhesive of this invention may be used, for example, in the transdermal drug delivery systems described in U.S. Pat. Nos. 4,840,796 and 4,951,657; and U.S. Patent Application Publications US2005/0048104 and US2007/0172518.

Coating Composition

The crosslinkable composition comprising starting materials (A), (B) and optionally (C), described above, may alternatively be used in a coating composition, e.g., for forming a coating on a substrate. The coating composition comprises: (a) the copolymer composition comprising starting materials (A), (B) and optionally (C), described above, and (b) a coating additive. The coating additive may be selected from (b1) a water scavenger, (b2) a pigment, (b3) a diluent, (b4) a filler, (b5) a rust inhibitor, (b6) a plasticizer, (b7) a thickening agent, (b8) a pigment dispersant, (b9) a flow aid, (b10) a solvent, (b11) an adhesion promoter, (b12) a catalyst, (b13) an organic co-binder, (b14) a siloxane co-binder, (b15) a matting agent, (b16) a leveling agent, (b17) a wax, (b18) a texturizing additive, (b19) an anti-scratching additive, (b20) a gloss modifying additive, (b21) a stabilizer, and (b22) a crosslinker, or a combination of two or more of (b1), (b2), (b3), (b4), (b5), (b6), (b7), (b8), (b9), (b10), (b11), (b12)(b13), (b14), (b15), (b16), (b17), (b18), (b19), (b20), (b21) and (b22). Suitable fillers include silica and titanium dioxide, or zirconium dioxide. Suitable adhesion promoters include alkoxysilanes such as 3-glycidoxypropyltrimethoxysilane. Suitable solvents are as described above in the method for making the copolymer. Examples of suitable (b2) pigments, (b3) diluents, (b4) fillers, (b5) rust inhibitors, (b6) plasticizers, (b7) thickening agents, (b8) pigment dispersants, (b9) flow aids, (b10) solvents, and (b11) adhesion promoters are disclosed in U.S. Patent Application Publication Number 2015/0031797 and PCT Publications WO2015/097064, WO2015/100258, and WO2016/126362. The catalyst used in the coating composition as starting material (b12) may be the same as described as starting material e) described above and may be present in the coating composition in an amount of 0.01% to 5.00% by weight based on combined weights of all starting materials used to make the composition. Starting material, (b13) is an organic co-binder such as a polyol, polyamine, or polyisocyanate; which can be added to the coating composition in an amount of 0 to 99% based on combined weights of all starting materials used to make the composition. Starting material (b14) is a siloxane co-binder that may be added in an amount of 0 to 99%, based on combined weights of all starting materials in the composition. Starting material (b15) is a matting agent that can be 0 to 30% based on combined weights of all starting materials in the composition. Starting material (b16) is a leveling agent, which can be present in an amount of 0 to 10% of the composition. Starting material, (b17) wax can comprise 0 to 20% of the composition described herein. Starting material, (b18) is a texturing additives that can be added to the composition in an amount of 0 to 20%. Starting materials (b19), (b20), (b21), and (b22) combined, can be 0 to 15%, all based on the total amount of all starting materials in the coating composition.

The coating composition may be crosslinked to form a coating such as a primer or a top coat on a substrate. The substrate can be a metal, glass, wood, painted layer, plastic foil, a fiber and/or textile, or leather. The coating composition can be applied to the substrate, e.g., fiber and/or textile during making the fibers or textiles, or later such as during laundering textiles. After application, solvent (if any) can be removed from the coating composition for example by drying the coating composition at ambient or elevated temperature. The amount of treatment composition applied to the substrate, e.g., fibers and textiles is typically sufficient to provide 0.1 to 15 weight percent of the composition on the substrate, based on the dry weight of the substrate, alternatively in an amount of 0.2 to 5 weight percent based on the dry weight of the substrate.

Fibers and textiles that can be treated with the treatment composition include natural fibers such as cotton, silk, linen, and wool; regenerated fibers such as rayon and acetate; synthetic fibers such as polyesters, polyamides, polyacrylonitriles, polyethylenes, and polypropylenes; combinations, and blends thereof. The form of the fibers can include threads, filaments, tows, yarns, woven fabrics, knitted materials, non-woven materials, paper, and carpet. For purposes of this application, additional substrates can be treated with the treatment composition, including leather. Without wishing to be bound by theory, it is thought that textiles treated with the silicone block copolymer have a feel on hand comparable to conventional hydrophobic silicone, but do not significantly impact negatively on the hydrophilicity of the textile. Without wishing to be bound by theory, it is thought that a coating formed from the coating composition described above may have one or more benefits of high gloss, flexibility, hardness, scratch resistance, and resistance to weathering, resistance to ultra-violet radiation exposure, or two or more thereof.

EXAMPLES

Some embodiments of the invention will now be described in detail in the examples below. Reference Examples are not prior art unless so indicated.

TABLE A

Abbreviations

| Abbreviation | Meaning |
|---|---|
| AA | Allyl amine from Aldrich |
| AOH | Allyl alcohol |
| BD | 1,4-butanediol |
| DA | Diallyl amine from TCI |
| TPDA | Trimethylol propane diallylether form Aldrich |
| DMA | N, N-dimethylacetamide |
| EtAc | Ethyl acetate, from Sigma-Aldrich. Anhydrous for polymerization reaction. HPLC grade for dissolving and processing copolymers. |
| EtOH | 200 Proof Ethanol from Aldrich. Used to ensure residual NCO is completely reacted. |
| HDI | Hexamethylene diisocyanate from Acros |
| MDI | Isonate 50 O,P' from The Dow Chemical Company |
| IPDI | Isophorone diisocyanate from Alfa Aesar |
| TDI | Toluene Diisocyanate |
| THF | Tetrahydrofuran |
| DBTL | Dibutyltin dilaurate from Aldrich |
| C16, | Carbinol terminated polydimethylsiloxane having MW of 920 to 924 from Gelest, Product DMS-C16 |
| C21 | Carbinol terminated polydimethylsiloxane having MW of 4330 to 4680 from Gelest, Product DMS-C21 |
| C23 | Carbinol terminated polydimethylsiloxane having MW of 12000 from Gelest, Product DMS-C23 |
| C62 | Carbinol terminated polydimethylsiloxane with a molecular weight MW of 1670 from Dow Corning |
| PEG400 | Polyethylene glycol having Mw of 400 from TCI |
| FTIR | Fourier Transform Infra-Red |
| NMR | Nuclear Magnetic Resonance |
| MI | Milliliters |
| ° C. | Degrees Celsius |
| Mg | Milligrams |
| Mn | Number average molecular weight determined by NMR |
| NMR | Nuclear magnetic resonance |
| XX-3035 | Trimethylsiloxy terminated dimethylsiloxane-methylmercaptopropylsiloxane copolymer with a SH content of 0.35 mol/100 g, made in the lab and analyzed by $^{29}$Si and $^1$H NMR. |
| SMS 142 | Trimethylsiloxy terminated dimethylsiloxane-methylmercaptopropylsiloxane copolymer with a SH content of 0.16 mol/100 g, purchased from Gelest, Inc. |
| SMS 042 | Trimethylsiloxy terminated dimethylsiloxane-methylmercaptopropylsiloxane copolymer with a SH content of 0.05 mol/100 g, purchased from Gelest, Inc. |
| 26298-125 SH crosslinker | Trimethylsiloxy terminated dimethylsiloxane-methylmercaptopropylsiloxane copolymer with a SH content of 0.16 mol/100 g, made in the lab and analyzed by $^{29}$Si and $^1$H NMR. |
| Darocur 1173 | 2-Hydroxy-2-methyl-1-phenyl-propan-1-one |
| N/A | Not available (not measured) |

Reference Examples 1—General Procedure for Preparing Copolymers

A ml 4 neck flask was placed into a temperature controlled heating block and fitted with mechanical stirrer, thermometer, dropping funnel and reflux condenser.

1) The flask was charged with an a) isocyanate compound and a b) polyorganosiloxane, which were mixed to form a mixture.

2) The mixture was stirred and heated at 60° C., and the progress of the reaction followed by FTIR.

Optionally 3) After a period of time, solvent was added and the reaction cooled to room temperature of 15° C. to 40° C.

4) An c) endblocker (and optionally e) solvent) were charged to the dropping funnel and added drop-wise to the mixture in the flask, which was then heated for a period of time.

5) The mixture in the flask was cooled to room temperature and filtered through a 0.45 micron filter using Celite® 545 filter aid. The filtrate was transferred into a round flask and volatiles removed with a rotary evaporator (90° C., 1 mbar).

Samples were prepared according to this procedure using starting materials and conditions shown in Table 1.

Reference Examples 2—General Procedure for Preparing Copolymers

A ml 4 neck flask was placed into a temperature controlled heating block and fitted with mechanical stirrer, thermometer, dropping funnel and reflux condenser.

1) The flask was charged with an a) isocyanate compound, an b) endblocker and a c) catalyst, which were mixed to form a mixture.

2) The mixture was stirred and heated at 60° C. for 1 hour, and the progress of the reaction followed by FTIR.

3) After a period of time the reaction was cooled to room temperature of 15° C. to 30° C. and solvent added.

4) A d) polyorganosiloxane and a e) polyethylene glycol (and optionally f) solvent) were charged to the dropping funnel and added drop-wise to the mixture in the flask, which was then heated for a period of time at 60° C.

5) f) EtOH was added to the mixture in the flask, which was then heated to reflux for period of time.

6) The mixture in the flask was cooled to room temperature and filtered through a 0.45 micron filter using Celite® 545 filter aid. The filtrate was transferred into a round flask and volatiles removed with a rotary evaporator (90° C., 1 mbar).

Samples were prepared according to this procedure using starting materials and conditions shown in Table 1.

TABLE 1

Copolymer Preparation

| Examples 1 | a) isocyanate compound | b) polyorganosiloxane | Time for heating in step 2) | Optional solvent in step 3) | Endblocker and optional solvent in step 4) | Temperature for heating in step 4) | Time for Heating in step 4) |
|---|---|---|---|---|---|---|---|
| 1 IPDI$_n$C21$_m$AA$_2$, (n, m) = (2, 1) | 17.8 g IPDI | 187.1 g C21 | 7.5 hours | 100 ml THF | 200 ml of anhydrous THF and 5.7 g of allyl amine | Boiled under reflux | 2 hours |
| 2 IPDI$_n$C16$_m$DA$_2$, (n, m) = (14, 13) | 22.23 g IPDI | 87.8 g C16 | 7.5 hours | No step 3) | 120 ml EtAc and 1.94 g diallyl amine | Heated at 70° C. | 2 hours |

TABLE 1-continued

Copolymer Preparation

| | | | | | | | |
|---|---|---|---|---|---|---|---|
| 3 IPDI$_n$C21$_m$DA$_2$; (n, m) = (2, 1) | 23.3 g IPDI | 245.5 C21 | 24 hours | 100 ml THF | 200 ml THF and 12.7 g diallyl amine | Boiled under reflux | 2 hours |
| 4 I$_n$C23$_m$AA$_2$; (n, m) = (2, 1) | 4.4 g IPDI | 120.0 g C23 | 30 hours | 100 ml THF | 200 ml THF and 1.4 g allyl amine | Boiled under reflux | 2 hours |
| 5 (comparative) IPDI$_n$C21$_m$AOH$_2$; (n, m) = (3, 2) | 20.0 g IPDI | 260.0 g C21 | 45 hours | No step 3) | 13.9 g allyl alcohol | Heated at 60° C. | 8 hours |
| 6 HDI$_n$C16$_m$DA$_2$; (n, m) = (14, 13) | 40.4 g HDI | 211.1 g C16 | 7 hours | No step 3) | 200 ml EtAc and 8.4 g diallyl amine | Heated at 70° C. | 2 hours |
| 7 HDI$_n$C21$_m$DA$_2$; (n, m) = (20, 19) | 4.3 g HDI | 105.2 g C21 | 22 hours | No step 3) | 200 ml EtAc and 0.5 g diallyl amine | Heated at 70° C. | 2 hours |
| 8 HDI$_n$C23$_m$DA$_2$; (n, m) = (5, 4) | 4.8 g HDI | 276.5 g C23 | 73 hours | No step 3) | 300 ml of EtAc and 0.5 g of diallyl amine | Heated at 70° C. | 2 hours |
| 9 HDI$_n$C62$_m$DA$_2$; (n, m) = (13, 12) | 10.4 g HDI | 97.9 g C62* | 35 minutes | No step 3) | 120 ml EtAc and 1.2 g diallyl amine | Heated at 70° C. | 2 hours |
| 10 (DA$_2$HDI$_n$C16$_m$)$_2$BD$_x$; (n, m, x) = (20, 18, 1) | 17.1 g HDI | 84.5 g C16 | 12 hours | No step 3)** | 60 ml of EtAc and 1.9 g of diallyl amine | Heated at 70° C. | 2 hours |
| 11 HDI$_n$C21$_m$DA$_2$; (n, m) = (3, 2) | 8.1 g HDI | 149.7 g C21 | 21 hours | No step 3) | 150 ml THF and 5.8 g diallyl amine | Boiled under reflux | 2 hours |
| 12 HDI$_n$C21$_m$DA$_2$; (n, m) = (7, 6) | 7.1 g HDI | 156.0 g C21 | 29 hours | No step 3) | 150 ml THF and 2.3 g diallyl amine | Boiled under reflux | 2 hours |
| 13 HDI$_n$C16$_m$DA$_2$; (n, m) = (10, 9) | 16.8 g HDI | 83.1 g C16 | 7 hours | No step 3) | 120 ml THF and 3.9 g diallyl amine | Boiled under reflux | 2 hours |
| 14 HDI$_n$C16$_m$DA$_2$; (n, m) = (15.75, 14.75) | 16.8 g HDI | 87.8 g C16 | 7 hours | No step 3) | 120 ml THF and 1.9 g diallyl amine | Boiled under reflux | 2 hours |
| 15 HDI$_n$C16$_m$DA$_2$; (n, m) = (16.6, 15.6) | 40.4 g HDI | 210.7 g C16 | 7 hours | No step 3) | 400 ml EtAc and 4.7 g diallyl amine | Heated at 70° C. | 2 hours |
| 16 HDI$_n$C16$_m$DA$_2$; (n, m) = (15, 14) | 16.8 g HDI | 94.6 g C16 | 7 hours | No step 3) | 120 ml THF and 1.9 g diallyl amine | Boiled under reflux | 2 hours |

| Examples 2 | a) isocyanate compound | b) Endblocker, c) Catalyst | d) polyorganosiloxane | e) polyethylene glycol f) Solvent | Time for Heating in step 4) | f) EtOH | Time for Heating in step 5) |
|---|---|---|---|---|---|---|---|
| 17 HDI$_n$C62$_m$PEG400$_o$TPDA$_2$; (n, m, o) = (14, 6.5, 6.5) | 16.6 g HDI | 3.2 g TPDA 0.08 g DBTL | 79.8 g C62 | 18.7 g PEG400 100 ml EtAc | 5 hours | 5 g EtOH | 2 hours |
| 18 MDI$_n$C62$_m$PEG400$_o$TPDA$_2$; (n, m, o) = (14.2, 6.6, 6.6) | 22.1 g MDI | 2.8 g TPDA 0.08 g DBTL | 71.6 gC62 | 16.8 g PEG400 100 ml EtAc | 4 hours | 5 g EtOH | 2 hours |

**In example 10, step 3) described above was not practiced. However, a chain extender was added after step 2). 0.46 g of 1,4-butanediol from Aldrich was added and reacted for an additional 3 hours at 60° C.

Table 2 shows the results of the examples in Table 1. The number average molecular weight (Mn) of each copolymer was measured by NMR. $^1$H-NMR analysis (in ppm, solvent CDCl$_3$) analysis (solvent CDCl$_3$) were perfomed.

TABLE 2

Copolymer Characterization Results

| Example | Molecular Weight (Mn) (g/mol) | $^1$H-NMR analysis | $^{13}$C-NMR analysis |
|---|---|---|---|
| 1 | 5200 | Olefinic (5.91-5.79, 5.22-5.10 ppm), NH (4.62-4.38), —CH$_2$OOC (4.20-4.17), —CH$_2$—CH═CH$_2$ (3.80-3.77), —CH (3.64-3.59), —CH$_2$—O— (3.61-3.58), —CH$_2$—O— (3.42-3.39), —CH$_2$—NHCO (2.96-2.89), —CH$_2$— (1.85-1.82, 1.73-1.56), —CH$_3$ (1.04, 0.91), —CH$_2$—Si (0.53-0.48), Si—CH$_3$ (0.09-0.03) | NHC═ONH, NHC═OO (159.52, 158.67, 157.36, 157.28, 156.16), —HC═CH$_2$ (136.40), —HC═CH$_2$ (115.56), —CH$_2$O— (74.40, 69.33), O—CH$_2$—HC═CH$_2$ (68.18), —CH$_2$OOC (64.18), —CH$_2$NHC═ONH (54.46), cyclic —CH$_2$—, —CH— (47.71, 46.73, 45.13, 42.40), —CH$_2$—HC═CH$_2$ (43.24), cyclic C (36.86, 35.39), —CH$_3$ (32.19, 28.06, 23.70), —CH$_2$— (23.87), Si—CH$_2$— (14.44), Si(CH$_3$)$_2$ (1.49, 1.38, 0.44) |

TABLE 2-continued

Copolymer Characterization Results

| Example | Molecular Weight (Mn) (g/mol) | ¹H-NMR analysis | ¹³C-NMR analysis |
|---|---|---|---|
| 2 | 14100 | Olefinic (5.85-5.73, 5.22-5.15 ppm), NH (4.68-4.40), —CH₂OOC (4.00-4.17), —CH₂—CH=CH₂ (3.86-3.84), —CH (3.81-3.72), —CH₂—OH (3.60-3.56), —CH₂—NHCO (3.06-2.98), —CH₂— (1.73-1.55), —CH₃ (1.04, 0.91), —CH₂—Si (0.54-0.50), Si—CH₃ (0.07-0.02) | NHC=ONH, NHC=OO (158.61, 158.49, 157.32), —HC=CH₂ (134.91, 134.81, 134.57), —HC=CH₂ (117.07, 117.00), —CH₂O— (67.69, 67.46), —CH₂OOC (65.31), —CH₂NHC=ONH (55.24), cyclic —CH₂—, —CH— (50.09, 47.46, 46.75, 42.29), —CH₂—HC=CH₂ (44.83), cyclic C (36.75, 32.14), —CH₃ (35.75, 27.96, 26.69), —CH₂— (23.33), Si—CH₂— (14.32), Si(CH₃)₂ (1.49, 1.38, 0.44) |
| 3 | 5300 | Olefinic (5.85-5.76, 5.21-5.16 ppm), NH (4.82-4.79, 4.54-4.50), —CH₂OOC (4.18-4.17), —CH₂—CH=CH₂ (3.86-3.85), —CH (3.81-3.76), —CH₂—O (3.61-3.58), —CH₂—O— (3.43-3.39), —CH₂—NHCO (2.98-2.89), —CH₂— (1.73-1.70, 1.62-1.56), —CH₃ (1.04, 1.01, 0.91, 0.86, 0.84), —CH₂—Si (0.53-0.49), Si—CH₃ (0.06-0.03) | NHC=ONH, NHC=OO (158.59, 158.50, 157.82, 157.16, 156.96), —HC=CH₂ (135.89, 134.98, 134.63), —HC=CH₂ (117.02, 116.93), —CH₂O— (74.46, 69.38), O—CH₂—HC=CH₂ (64.40), —CH₂OOC (64.17), —CH₂NHC=ONH (55.98, 54.72), cyclic —CH₂—, —CH— (50.12, 49.71, 47.69, 46.81, 45.03), —CH₂—HC=CH₂ (42.34), cyclic C (36.74, 35.46), —CH₃ (32.16, 28.00, 23.84), —CH₂— (23.71), Si—CH₂— (14.43), Si(CH₃)₂ (1.63-0.44) |
| 4 | 19400 | Olefinic (5.91-5.79, 5.22-5.12 ppm), NH (4.58-4.37), —CH₂OOC (4.21-4.18), —CH₂—CH=CH₂ (3.81-3.78), —CH (3.64-3.59), —CH₂—O (3.61-3.58), —CH₂—O (3.45-3.39), —CH₂—NHCO (2.95-2.9), —CH₂— (1.74-1.57), —CH₃ (1.06, 0.92, 0.88, 0.82), —CH₂—Si (0.54-0.49), Si—CH₃ (0.07-0.05) | NHC=ONH, NHC=OO (159.20, 158.55, 157.22, 156.14), —HC=CH₂ (136.37), —HC=CH₂ (115.88), —CH₂O— (75.53, 69.39), ), O—CH₂—HC=CH₂ (68.22), —CH₂OOC (64.23), —CH₂NHC=ONH (54.50), cyclic —CH₂—, —CH— (47.79, 46.77, 45.16, 43.50), —CH₂—HC=CH₂ (42.53), cyclic C (36.86, 35.52), —CH₃ (32.22, 28.09, 25.98), —CH₂— (23.72), Si—CH₂— (14.46), Si(CH₃)₂ (1.64-0.47) |
| 5 | 9450 | Olefinic (5.96-5.86, 5.32-5.18 ppm), NH (4.83-4.71, 4.55-4.52), —CH₂—CH=CH₂ (4.55-4.52), —CH₂OOC (4.21-4.17), —CH (3.84-3.69), —CH₂—O— (3.61-3.58), —CH₂—O (3.43-3.39), —CH₂—NHCO (2.92-2.89), —CH₂— (1.73-1.69, 1.64-1.56), —CH₃ (1.05, 1.04, 0.91, 0.87, 0.83), —CH₂— Si (0.53-0.48), Si—CH₃ (0.06-0.03) | NHC=ONH, NHC=OO (157.16, 157.01, 155.97), —HC=CH₂ (117.90), —CH₂O— (74.43, 69.37), O—CH₂—HC=CH₂ (65.87), —CH₂OOC (64.17), —CH₂NHC=ONH (55.25), cyclic —CH₂—, —CH— (47.94, 47.44, 46.67, 44.97), —CH₂—HC=CH₂ (42.20), cyclic C (36.78, 35.41), —CH₃ (32.16, 27.97, 23.71), —CH₂— (23.61), Si—CH₂— (14.44), Si(CH₃)₂ (1.61-0.44) |
| 6 | 20700 | Olefinic (5.83-5.73, 5.19-5.13 ppm), NH (4.64, 4.43), —CH₂OOC (3.99-3.96), —CH₂—CH=CH₂ (3.84-3.82), —CH₂—OH (3.59-3.56), —CH₂—NHCO (3.20-3.11), —CH₂— (1.64-1.58, 1.50-1.45, 1.33-1.30), —CH₂—Si (0.54-0.49), Si—CH₃ (0.07-0.02) | NC=ONH, NHC=OO (158.51, 157.15), —HC=CH₂ (134.69), —HC=CH₂ (116.88), —CH₂OOC (67.51), N—CH₂—HC=CH₂ (49.71), —CH₂NHC=OO CH₂NHC=ON (41.09, 40.88), —CH₂— (30.47, 30.31, 26.63), —CH₂— (23.34), Si—CH₂— (14.32), Si(CH₃)₂ (1.47-0.42) |
| 7 | 23000 | Olefinic (5.83-5.74, 5.19-5.14 ppm), NH (4.73, 4.43), —CH₂OOC (4.20-4.18), —CH₂—CH=CH₂ (3.84-3.83), —CH₂—O (3.60-3.58), —CH₂—O (3.42-3.39), —CH₂—NHCO (3.16-3.11), —CH₂— (1.64-1.56, 1.50-1.44, 1.32-1.29), —CH₂—Si (0.53-0.48), Si—CH₃ (0.10-0.03) | NC=ONH, NHC=OO (158.57, 156.81), —HC=CH₂ (133.38), —HC=CH₂ (117.90), —CH₂O— (74.50, 69.43), —CH₂OOC (64.95), N—CH2—HC=CH2 (49.84), —CH₂NHC=OO CH₂NHC=ON (41.23), —CH₂— (30.26, 26.66) —CH₂— (23.72), Si—CH₂— (14.45), Si(CH₃)₂ (1.69-0.47) |
| 8 | 49000 | NC=ONH, NHC=OO (158.56, 156.81), —HC=CH₂ (134.77), —HC=CH₂ (116.92), —CH₂O— (74.47, 69.44), —CH₂OOC (64.30), N—CH₂—HC=CH₂ (49.84), —CH₂NHC=OO —CH₂NHC=ON (41.20, 40.91), —CH₂— (31.16, 30.52, 30.27, 26.62) —CH₂— (23.72), Si—CH₂— (14.46), Si(CH₃)₂ (1.66-0.45 | NC=ONH, NHC=OO (158.56, 156.81), —HC=CH₂ (134.77), —HC=CH₂ (116.92), —CH₂O— (74.47, 69.44), —CH₂OOC (64.30), N—CH₂—HC=CH₂ (49.84), —CH₂NHC=OO —CH₂NHC=ON (41.20, 40.91), —CH₂— (31.16, 30.52, 30.27, 26.62) —CH₂— (23.72), Si—CH₂— (14.46), Si(CH₃)₂ (1.66-0.45 |
| 9 | 21700 | Olefinic (5.83-5.73, 5.19-5.14 ppm), NH (4.74, 4.42), —CH₂OOC (4.19-4.17), —CH₂—CH=CH₂ (3.84-3.82), CH₂—OH (3.79-3.78), CH₂—CH₂—OH (3.52-3.48), —CH₂—O (3.60-3.58), —CH₂—O (3.42-3.39), —CH₂—NHCO (3.21-3.11), —CH₂— (1.64-1.56, 1.50-1.44, 1.33-1.29), —CH₂—Si (0.53-0.48), Si—CH₃ (0.09-0.03). | NC=ONH, NHC=OO (158.50, 156.80), —HC=CH₂ (134.72), —HC=CH₂ (116.87), —CH₂O— (74.40, 69.38), —CH₂OOC (64.23), N—CH₂—HC=CH₂ (49.73), —CH₂NHC=OO —CH₂NHC=ON (41.15, 40.89), —CH₂— (31.15, 30.48, 30.21, 26.60) —CH₂— (23.69), Si—CH₂— (14.41), Si(CH₃)₂ (1.64-0.44 |
| 10 | 21900 | Olefinic (5.83-5.73, 5.18-5.14 ppm), NH (4.64, 4.43), —CH₂OOC (3.99-3.96), —CH₂—CH=CH₂ (3.84-3.82), —CH₂—OH (3.59-3.56), —CH₂—NHCO (3.16-3.11), —CH₂— (1.64-1.56, 1.50-1.45, 1.33-1.30), —CH₂—Si (0.54-0.49), Si—CH₃ (0.06-0.03) | NC=ONH, NHC=OO (158.49, 157.14), —HC=CH₂ (134.65), —HC=CH₂ (116.87), —CH₂OOC (67.49), —CH₂—OCO (65.30), N—CH₂—HC=CH₂ (49.66), —CH₂NHC=OO CH₂NHC=ON (41.70, 41.09), —CH₂— (30.70, 30.30, 26.63, 26.11), —CH₂— (23.32), Si—CH₂— (14.29), Si(CH₃)₂ (1.35-0.40). |

TABLE 2-continued

Copolymer Characterization Results

| Example | Molecular Weight (Mn) (g/mol) | $^1$H-NMR analysis | $^{13}$C-NMR analysis |
|---|---|---|---|
| 11 | 10200 | Olefinic (5.83-5.75, 5.20-5.16 ppm), NH (4.75, 4.43), —CH$_2$OOC (4.20), —CH$_2$—CH=CH$_2$ (3.85-3.84), —CH$_2$—O— (3.60), —CH$_2$—O— (3.44-3.40), —CH$_2$—NHCO (3.21-3.13), —CH$_2$— (1.65-1.58, 1.48-1.46, 1.32), —CH$_2$—Si (0.54-0.50), Si—CH$_3$ (0.07-0.04). | N—C=O—NH, NH—C=O—O (158.53, 156.81), —HC=CH$_2$ (134.76), —HC=CH$_2$ (116.90), —CH$_2$O— (74.45, 69.42), —CH$_2$O—CO (64.26), N—CH$_2$—HC=CH$_2$ (49.79), —CH$_2$—NH—C=O—O CH$_2$—NH—C=O—N (41.19, 40.91), —CH$_2$— (30.51, 30.25, 26.63) —CH$_2$— (23.72), Si—CH$_2$— (14.44), Si(CH$_3$)$_2$ (1.69-0.47). |
| 12 | 18400 | Olefinic (5.84-5.75, 5.20-5.15 ppm), NH (4.75, 4.42), —CH$_2$OOC (4.20-4.18), —CH$_2$—CH=CH$_2$ (3.85-3.83), —CH$_2$—O— (3.61-3.59), —CH$_2$—O— (3.43-3.39), —CH$_2$—NHCO (3.21-3.12), —CH$_2$— (1.65-1.57, 1.49-1.44, 1.33-1.29), —CH$_2$—Si (0.53-0.49), Si—CH$_3$ (0.11-0.01). | N—C=O—NH, NH—C=O—O (158.53, 156.81), —HC=CH$_2$ (134.21), —HC=CH$_2$ (116.39), —CH$_2$O— (74.98, 69.64), —CH$_2$O—CO (64.81), N—CH$_2$—HC=CH$_2$ (49.21), —CH$_2$—NH—C=O—O CH$_2$—NH—C=O—N (41.67, 40.82), —CH$_2$— (30.86, 30.72, 26.53) —CH$_2$— (23.59), Si—CH$_2$— (14.35), Si(CH$_3$)$_2$ (1.68-0.44). |
| 13 | 18900 | Olefinic (5.83-5.73, 5.19-5.13 ppm), NH (4.63, 4.43), —CH$_2$OOC (3.99-3.96), —CH$_2$—CH=CH$_2$ (3.84-3.82), —CH$_2$—OH (3.60-3.56), —CH$_2$—NHCO (3.20-3.11), —CH$_2$— (1.64-1.56, 1.50-1.45, 1.33-1.30), —CH$_2$—Si (0.54-0.49), Si—CH$_3$ (0.08-0.03). | N—C=O—NH, NH—CO—O (158.21, 157.45), —HC=CH$_2$ (134.31), —HC=CH$_2$ (116.82), —CH$_2$O—CO (67.61), N—CH$_2$—HC=CH$_2$ (49.43), —CH$_2$—NH—C=O—O CH$_2$—NH—C=O—N (41.39, 40.66), —CH$_2$— (30.73, 30.51, 26.49), —CH$_2$— (23.32), Si—CH$_2$— (14.38), Si(CH$_3$)$_2$ (1.46-0.48). |
| 14 | 16500 | Olefinic (5.83-5.73, 5.19-5.13 ppm), NH (4.63, 4.43), —CH$_2$OOC (3.99-3.96), —CH$_2$—CH=CH$_2$ (3.84-3.82), —CH$_2$—OH (3.60-3.56), —CH$_2$—NHCO (3.20-3.11), —CH$_2$— (1.64-1.56, 1.50-1.45, 1.33-1.30), —CH$_2$—Si (0.54-0.49), Si—CH$_3$ (0.10-0.02). | N—C=O—NH, NH—CO—O (158.41, 157.39), —HC=CH$_2$ (134.49), —HC=CH$_2$ (116.71), —CH$_2$O—CO (67.85), N—CH$_2$—HC=CH$_2$ (49.62), —CH$_2$—NH—C=O—O CH$_2$—NH—C=O—N (41.47, 40.82), —CH$_2$— (30.59, 30.29, 26.42), —CH$_2$— (23.41), Si—CH$_2$— (14.17), Si(CH$_3$)$_2$ (1.43-0.44). |
| 15 | 17500 | Olefinic (5.83-5.73, 5.18-5.13 ppm), NH (4.63, 4.43), —CH$_2$OOC (3.99-3.96), —CH$_2$—CH=CH$_2$ (3.84-3.82), —CH$_2$—OH (3.60-3.56), —CH$_2$—NHCO (3.16-3.11), —CH$_2$— (1.64-1.56, 1.49-1.45, 1.33-1.30), —CH$_2$—Si (0.54-0.49), Si—CH$_3$ (0.09-0.02). | N—C=O—NH, NH—CO—O (158.69, 157.52), —HC=CH$_2$ (134.75), —HC=CH$_2$ (116.93), —CH$_2$O—CO (67.79), N—CH$_2$—HC=CH$_2$ (49.64), —CH$_2$—NH—C=O—O CH$_2$—NH—C=O—N (41.58, 40.97), —CH$_2$— (30.63, 30.27, 26.54), —CH$_2$— (23.62), Si—CH$_2$— (14.28), Si(CH$_3$)$_2$ (1.46-0.42). |
| 16 | 16900 | Olefinic (5.83-5.73, 5.19-5.14 ppm), NH (4.63, 4.43), —CH$_2$OOC (3.99-3.96), —CH$_2$—CH=CH$_2$ (3.84-3.82), —CH$_2$—OH (3.60-3.56), —CH$_2$—NHCO (3.20-3.11), —CH$_2$— (1.64-1.56, 1.49-1.45, 1.33-1.30), —CH$_2$—Si (0.54-0.49), Si—CH$_3$ (0.08-0.03). | N—C=O—NH, NH—CO—O (158.57, 157.31), —HC=CH$_2$ (134.42), —HC=CH$_2$ (116.93), —CH$_2$O—CO (67.45), N—CH$_2$—HC=CH$_2$ (49.52), —CH$_2$—NH—C=O—O CH$_2$—NH—C=O—N (41.17, 40.79), —CH$_2$— (30.69, 30.43, 26.58), —CH$_2$— (23.27), Si—CH$_2$— (14.26), Si(CH$_3$)$_2$ (1.45-0.46). |
| 17 | 16500 | Olefinic (5.88-5.80, 5.25-5.10 ppm), NH (4.91, 4.36), —CH$_2$OOC (4.19-4.17), COO—CH$_2$—C(Et)— (4.00), {Vi—CH$_2$}$_2$—O— (3.93-3.90), —CH$_2$—OCH$_2$CH$_2$O—CH$_2$— —CH$_2$—O—C$_3$H$_6$—Si (3.71-3.58), —O—CH$_2$—C$_3$H$_6$—Si (3.42-3.38), {Allyl—O—CH$_2$}$_2$— (3.29), —CH$_2$—NHCO (3.16-3.11), —CH$_2$— (1.63-1.55, 1.48-1.45, 1.32-1.29), C—CH$_2$—CH$_3$ (0.86-0.82), C—CH$_2$—Si (0.52-0.48), Si—CH$_3$ (0.08-0.03). | NH—CO—O (158.76), —HC=CH$_2$ (135.27), —HC=CH$_2$ (116.37), O—CH$_2$—C$_2$H$_4$—Si (74.14), Vi—CH$_2$—O (72.37), —(O—CH$_2$—CH$_2$)$_n$—O— (70.72), Allyl—O—CH$_2$— (69.80), —CH$_2$—(O—C$_2$H$_4$)$_n$—O—CH$_2$— (69.19), ≡C—CH$_2$—O—CO—NH— 65.09, —CH$_2$—CH$_2$—(O—C$_2$H$_4$)$_n$—O—CH$_2$—CH$_2$— (63.89), —OC—O—CH$_2$—CH$_2$—O—C$_3$H$_6$—Si (61.69), Et—C≡ (42.65), —C$_4$H$_8$—CH$_2$—NH—C=O—O (41.94, 41.56), —CH$_2$— (30.69, 26.47) 26.58), —CH$_2$—CH$_2$—O—Si (23.51), CH$_3$—CH$_2$—C≡ (23.09), Si—CH$_2$— (14.23), CH$_3$—CH$_2$—C≡ (7.79), Si—CH$_3$ (1.16-0.27). |
| 18 | 17900 | Aromatic (7.74-7.71, 7.29-7.20, 7.08-7.03, 6.71-6.68, 6.46-6.38), Olefinic (5.90-5.80, 5.25-5.10 ppm), —CH$_2$OOC (4.28-4.25, COO—CH$_2$—C(Et)— (4.12), {Vi—CH$_2$}$_2$—O— (3.93-3.92), Ph—CH$_2$—Ph (3.89-3.85), —CH$_2$—OCH$_2$CH$_2$O—CH$_2$— —CH$_2$—O—C$_3$H$_6$—Si (3.71-3.58), —O—CH$_2$—C$_3$H$_6$—Si (3.45-3.41), {Allyl—O—CH$_2$}$_2$— (3.33), —CH$_2$—NHCO (3.16-3.11), —CH$_2$— (1.65-1.58), C—CH$_2$—CH$_3$ (1.48-1.42), C—CH$_2$—CH$_3$ (0.88-0.84), C—CH$_2$—Si (0.54-0.49), Si—CH$_3$ (0.08-0.03). | NH—CO—O (154.40, 154.02), Aromatic (137.20-136.02), HC=CH$_2$ (135.30), Aromatic (133.97, 132.55, 132.31, 130.69, 129.49, 127.54, 125.11, 123.46, 123.35, 119.28), —HC=CH$_2$ (116.65), O—CH$_2$—C$_2$H$_4$—Si (74.31), Vi—CH$_2$—O (72.53), —(O—CH$_2$—CH$_2$)$_n$—O— (70.74), Allyl—O—CH$_2$— (69.68), —CH$_2$—(O—C$_2$H$_4$)$_n$—O—CH$_2$— (69.13), ≡C—CH$_2$—O—CO—NH— 65.70, —CH$_2$—CH$_2$—(O—C$_2$H$_4$)$_n$—O—CH$_2$—CH$_2$— —OC—O—CH$_2$—CH$_2$—O—C$_3$H$_6$—Si (64.62, 64.31), —OC—O—CH$_2$—CH$_2$—O—C$_3$H$_6$—Si (61.97, 61.78), Et—C≡ 42.78, —Ph—CH$_2$—Ph— (40.84, 37.27), —CH$_2$—CH$_2$—Si (23.65), CH$_3$—CH$_2$—C≡ (23.25), —CH$_2$—Si (14.38), CH$_3$—CH$_2$—C≡ (7.94), Si(CH$_3$)$_2$ (1.30-0.4). |

Samples of the copolymers described above were crosslinked.

Example 19—Composition Using the Copolymer of Example 1 (IPDI$_2$C21AA$_2$) and Different SH Crosslinkers A 2.5 g sample of the copolymer of Example 1 was placed in a cup and 0.213 g of a crosslinker was added to it. 0.1 wt % of Darocur 1173 (photoinitiator) was added to the cup, and the contents of the cup were hand mixed followed by mixing for 25 sec at 3000 rpm. The resulting composition was poured on a polyurethane sheet reinforced on Mylar, and a laminate was prepared using a 15 mil thick chase. This laminate was cured in a UV chamber for a period of time. A blue LDPE release liner was then rolled over the cured laminate, and the laminate was kept overnight at room temperature before it was tested for adhesion, release and cohesive strength. Each laminate was tested on the Texture Analyzer as per the following procedure.

For the release measurement, the release liner was secured in the bottom clamp, and the adhesive coated polyurethane laminate was secured in the top clamp. The clamps were pulled apart at 10 mm/s for 130 mm. The value reported for each strip was the average force (N)/in to pull the release liner from the adhesive coated polyurethane laminate. The data from the first 20 mm and the last 10 mm were discarded, and the data from the remaining 100 mm was averaged. One to three replicates were tested to generate the value reported in the table in Newtons per (linear) inch (N/in). The final reported value is the average of the 1 to 3 test strips (1 inch=~25 mm).

For the adhesion measurement, the release liner was removed from the coated test strip, and the test strip was adhered to the frosted side of a 1.5 in x 9 in (3.8 cm×23 cm) strip of polycarbonate. With the use of a 5 lb rubber coated roller, the adhesive strip was applied to the polycarbonate with one stroke forward and one stroke back at a rate of 1 in/sec (2.5 cm/sec). The sample was allowed to remain in contact with the polycarbonate for 30 minutes. During the test, the polycarbonate was secured in the bottom clamp, while the adhesive coated polyurethane was secured in the top clamp. As in the release test, the clamps were pulled apart at 10 mm/s for 130 mm. The force to pull the adhesive coated polyurethane (1 in wide) from the polycarbonate was averaged over 100 mm (excluding the first 20 mm and last 10 mm of the 130 mm pull) with the final measurement in Newtons per (linear) inch (N/in). The final reported value was the average of 1 to 3 test strips.

Percent cohesive failure was approximated by visually estimating the amount of adhesive remaining on the polycarbonate after testing for adhesion. When possible a distinction was made between cohesively failing through the adhesive (true cohesive failure) versus transferring from the polyurethane support to the polycarbonate (adhesive failure at the support). Any adhesive remaining on the polycarbonate was referred to as indicating cohesive failure.

Samples of compositions were prepared as above using the copolymer of Example 1 but varying SH:Vi ratio, SH cross linkers (SMS 142 and SMS 042), amounts of photoinitiator, and cure time. Laminates were prepared from all these compositions, which were tested on the Texture Analyzer for adhesion, release and cohesive strength as described above. The crosslinker used and amount of photoinitiator, as well as the test results, are shown below in Table 3.

Example 20—Composition Using the Copolymer of Example 4 (IPDI$_2$C23$_1$AA$_2$) and SMS 142 SH Crosslinker Example 19 was repeated, except a 2 g sample of the copolymer of Example 4 was placed in a cup with the 0.223 g of crosslinker and Darocur 1173. The laminates were tested on the Texture Analyzer following the procedure described in Example 19.

Samples of compositions were prepared as above using the copolymer of Example 4 but varying SH:Vi ratio, SH cross linkers (SMS 142 and SMS 042), amounts of photoinitiator, and cure time. Laminates were prepared from all these compositions, which were tested on the Texture Analyzer for adhesion, release and cohesive strength as described above. The crosslinker used and amount of photoinitiator, as well as the test results, are shown below in Table 3.

Example 21—Compositions Using the Copolymer of Example 11 (HDI$_3$C21$_2$DA$_2$) and SMS 142 and SMS 042 SH Cross Linkers Example 19 was repeated, except a 2 g of sample of the copolymer of Example 11 was placed in the cup, and 0.433 gm of crosslinker was added to it. The laminates were tested on the Texture Analyzer following the procedure described in Example 19.

Samples of compositions were prepared as above using the copolymer of Example 11 but varying SH:Vi ratio, SH cross linkers (SMS 142 and SMS 042), amounts of photoinitiator, and cure time. Laminates were prepared from all these compositions, which were tested on the Texture Analyzer for adhesion, release and cohesive strength as described above. The crosslinker used and amount of photoinitiator, as well as the test results, are shown below in Table 3.

Example 22—Composition Using the Copolymer of Example 5 (IPDI$_3$C21$_2$AOH$_2$) and SMS 142 and SMS 042 and SMS142 Mixed SH Cross Linkers Example 19 was repeated except a 2 g sample of the copolymer of Example 5 was placed in the cup with either one crosslinker or a combination of crosslinkers. The laminates were tested on the Texture Analyzer following the procedure described in Example 19.

Samples of compositions were prepared as above using the copolymer of Example 5 but varying SH:Vi ratio, SH cross linkers (SMS 142 and SMS 042), amounts of photoinitiator, and cure time. Laminates were prepared from all these compositions, which were tested on the Texture Analyzer for adhesion, release and cohesive strength as described above. The crosslinker used and amount of photoinitiator, as well as the test results, are shown below in Table 3.

Example 23—Compositions Using the Copolymer of Example 12 HDI$_7$C21$_6$DA$_2$ Polymer and SMS 142 SH Cross Linker Samples were prepared as in Example 19, except the copolymer added to the cup was replaced with 5 g of the copolymer of Example 12 and 0.0500 g of SMS142 SH crosslinker was added to it. The laminates were tested on the Texture Analyzer following the procedure described in Example 19.

Samples of compositions were prepared as above using the copolymer of Example 12 but varying SH:Vi ratio, SH cross linkers (SMS 142 and SMS 042), amounts of photoinitiator, and cure time. Certain compositions were also prepared as above but adding 5% aqueous dispersion of an active ingredient (Acetylsalicylic acid or Lidocaine, designated 23 A or 23 L, respectively). Laminates were prepared from all these compositions, which were tested on the Texture Analyzer for adhesion, release and cohesive strength as described above. The crosslinker used and amount of photoinitiator, as well as the test results, are shown below in Table 3.

Example 24—Compositions Using the Copolymer of Example 13 $HDI_{10}C16_9DA_2$ Polymer with SMS142 SH Cross Linker Samples were prepared as in Example 19, except that 8 g of the copolymer of Example 13 and 1.7305 g of SMS142 SH crosslinker were added to the cup. The laminates were tested on the Texture Analyzer following the procedure described in Example 19.

Samples of compositions were prepared as above using the copolymer of Example 13 but varying SH:Vi ratio and cure time. Laminates were prepared from all these compositions, which were tested on the Texture Analyzer for adhesion, release and cohesive strength as described above. The crosslinker used and amount of photoinitiator, as well as the test results, are shown below in Table 3.

Example 25—Compositions Using the Copolymer of Example 7 $HDI_{20}C21_{19}DA_2$ Polymer with SMS142 SH Cross Linker Example 19 was repeated, except that 8 g of the copolymer of Example 7 and 0.0662 m of SMS142 SH crosslinker were added to the cup The laminates were tested on the Texture Analyzer following the procedure described in Example 19.

Samples of compositions were prepared as above using the copolymer of Example 7 but varying SH:Vi ratio. Laminates were prepared from all these compositions, which were tested on the Texture Analyzer for adhesion, release and cohesive strength as described above. The crosslinker used and amount of photoinitiator, as well as the test results, are shown below in Table 3.

Example 26—Compositions Using the Copolymer of Example 14 $HDI_{15.75}C16_{14.75}DA_2$ Polymer with SMS142 SH Cross Linker and Series of Acrylates Crosslinkers Samples were prepared as in Example 19, except that 2.5 g of the Copolymer of Example 14 and 0.1250 g of pentaerythritol tetraacrylate crosslinker were added to the cup. The laminates were tested on the Texture Analyzer following the procedure described in Example 19.

Samples of compositions were prepared as above using the copolymer of Example 14 but varying the crosslinker selection and amount, the cure time, and SH:Vi ratio. Laminates were prepared from all these compositions, which were tested on the Texture Analyzer for adhesion, release and cohesive strength as described above. The crosslinker used and amount of photoinitiator, as well as the test results, are shown below in Table 3.

Example 27—Compositions Using the Copolymer of Example 15 $HDI_{16.6}C16_{15.6}DA_2$ Polymer with Pentaerythritol Tetraacrylate Crosslinker A 2.5 g sample of the copolymer of Example 15 was taken in a dental mixer cup and 0.1250 gm of pentaerythritol tetraacrylate crosslinker was added to it. 0.1 wt % of Darocur 1173 (photoinitiator) was added to the mixture and the mixture was hand mixed with a spatula followed by a dental mixer mixing for 25 sec at 3000 rpm. This formulation was then poured on a polyurethane sheet reinforced on Mylar and a laminate was prepared using a 15 mil thick chase. This laminate was cured in a UV chamber until completely cured. A blue LDPE release liner was then rolled over the cured laminate and the laminate was kept overnight at room temperature before it was tested for adhesion, release and cohesive strength. The laminates were tested on the Texture Analyzer following the procedure described in Example 19.

Compositions were prepared using this copolymer and acrylate while changing the amount of acrylate and photoinitiator. Laminates were prepared and cured in UV chamber until fully cured and tested on TA for adhesion and release. The crosslinker used and amount of photoinitiator, as well as the test results, are shown below in Table 3.

Example 28—Compositions Using the Copolymer of Example 16 $HDI_{15}C16_{14}DA_2$ Polymer with SMS142 and 26298-125 Dow Corning SH Cross Linkers Samples were prepared as in Example 19, except that 5 g of the copolymer of Example 16 and 0.6409 g of 26298-125 Dow Corning SH crosslinker were added to the cup. The laminates were tested on the Texture Analyzer following the procedure described in Example 19.

Samples of compositions were prepared as above using the copolymer of Example 16 but varying SH:Vi ratio, SH cross linkers, amounts of photoinitiator, and cure time. Laminates were prepared from all these compositions, which were tested on the Texture Analyzer for adhesion, release and cohesive strength as described above. The crosslinker used and amount of photoinitiator, as well as the test results, are shown below in Table 3.

TABLE 3

Crosslinking Conditions and Results

| Example | SH:Vi molar ratio | Photoinitiator % | Crosslinker | Cure Time (sec) | Adhesion (N/in) | Release (N/in) |
|---|---|---|---|---|---|---|
| 19 | 1 | 0.1 | XX-3035 | 5 | 0.027 | 0.000 |
| 19 | 1 | 1 | XX-3035 | 10 | 0.140 | 0.000 |
| 19 | 1 | 0.1 | SMS142 | 10 | 0.651 | 0.028 |
| 19 | 1 | 1 | SMS142 | 5 | 0.483 | 0.011 |
| 19 | 1 | 0.1 | XX-3035 | 5 | 0.444 | 0.004 |
| 19 | 1 | 1 | XX-3035 | 5 | 0.195 | 0.000 |

TABLE 3-continued

Crosslinking Conditions and Results

| Example | SH:Vi molar ratio | Photoinitiator % | Crosslinker | Cure Time (sec) | Adhesion (N/in) | Release (N/in) |
|---|---|---|---|---|---|---|
| 19 | 1 | 0.1 | SMS142 | 5 | 0.701 | 0.057 |
| 19 | 1 | 1 | SMS142 | 5 | 2.340 | 0.016 |
| 19 | 1 | 0.1 | SMS042 | 55 | 0.580 | 0.009 |
| 19 | 1 | 1 | SMS042 | 40 | 0.971 | 0.011 |
| 19 | 1 | 1 | SMS142 | 5 | 1.043 | 0.029 |
| 19 | 1.1 | 1 | SMS142 | 5 | 1.862 | 0.045 |
| 19 | 1.2 | 1 | SMS142 | 5 | 1.666 | 0.032 |
| 19 | 1.3 | 1 | SMS142 | 5 | 1.329 | 0.042 |
| 19 | 1.4 | 1 | SMS142 | 5 | 1.534 | 0.020 |
| 19 | 1.5 | 1 | SMS142 | 5 | 1.282 | 0.015 |
| 19 | 1.4 | 1 | SMS142 | 3 | 0.837 | 0.034 |
| 19 | 1.4 | 1 | SMS142 | 7 | 0.611 | 0.027 |
| 19 | 1.4 | 1 | SMS142 | 10 | 0.221 | 0.003 |
| 20 | 1.3 | 1 | SMS142 | 5 | 0.333 | 0.061 |
| 20 | 1.4 | 1 | SMS142 | 5 | 0.776 | 0.025 |
| 20 | 1.5 | 1 | SMS142 | 5 | 0.279 | 0.01 |
| 20 | 1.1 | 1 | SMS142 | 5 | 0.651 | 0.082 |
| 20 | 1.1 | 1 | SMS142 | 5 | 1.306 | 0.039 |
| 20 | 1.1 | 1 | SMS142 | 15 | 0.084 | 0.005 |
| 20 | 1.2 | 1 | SMS142 | 5 | 0.963 | 0.045 |
| 20 | 1.2 | 1 | SMS142 | 15 | 0.125 | 0.011 |
| 20 | 1.4 | 1 | SMS142 | 5 | 1.547 | 0.035 |
| 20 | 1.4 | 1 | SMS142 | 15 | 0.051 | 0.007 |
| 21 | 0.9 | 1 | SMS142 | 7 | 0.109 | 0.007 |
| 21 | 0.9 | 1 | SMS142 | 15 | 0.019 | 0.003 |
| 21 | 1 | 1 | SMS142 | 7 | 0.090 | 0.008 |
| 21 | 1 | 1 | SMS142 | 15 | 0 | 0 |
| 21 | 1.1 | 1 | SMS142 | 7 | 0.022 | 0.001 |
| 21 | 0.3 | 1 | SMS042 | 30 & 40 | 0.524 | 0.105 |
| 21 | 0.3 | 1 | 26298-125 | 60 & 80 | 2.810 | 0.156 |
| 22 | 1 | 1 | SMS142 | 7 | NA | NA |
| 22 | 1.1 | 1 | SMS142 | 7 | NA | NA |
| 22 | 1.2 | 1 | SMS142 | 7 | NA | NA |
| 22 | 1.3 | 1 | SMS142 | 7 | NA | NA |
| 22 | 1.4 | 1 | SMS142 | 7 | NA | NA |
| 22 | 1.5 | 1 | SMS142 | 7 | NA | NA |
| 22 | 1 | 1 | 3 SMS142: 1 SMS042 * | 10 | NA | NA |
| 22 | 1 | 1 | 2 SMS142: 1 SMS042 * | 10 | NA | NA |
| 22 | 1 | 1 | 1 SMS142: 1 SMS042 * | 13 | NA | NA |
| 22 | 1 | 1 | 0.5 SMS142: 1 SMS042 * | 17 | NA | NA |
| 23 | 0.9 | 1 | SMS142 | 7 | NA | NA |
| 23 | 1 | 1 | SMS142 | 7 | NA | NA |
| 23 | 1.1 | 1 | SMS142 | 7 | NA | NA |
| 23 | 0.3 | 1 | SMS142 | 10 | NA | NA |
| 23 | 0.5 | 1 | SMS142 | 7 | NA | NA |
| 23 | 0.7 | 1 | SMS142 | 7 | NA | NA |
| 23 | 0.5 | 1 | SMS142 | 15 | 0.932 | 0.038 |
| 23 | 0.7 | 1 | SMS142 | 15 | 0.340 | 0.014 |
| 23 | 0.9 | 1 | SMS142 | 15 | 0.177 | 0.008 |
| 23 | 0.1 | 1 | SMS142 | 70 & 160 | NA | 0.437 |
| 23 | 0.25 | 1 | SMS142 | 30 | 1.071 | 0.07 |
| 23 A | 0.5 | 1 | SMS142 | 50 | 0.431 | 0.041 |
| 23 A | 0.7 | 1 | SMS142 | 30 | 0.195 | 0.002 |
| 23 L | 0.5 | 1 | SMS142 | 30 | 0.491 | 0.019 |
| 23 L | 0.7 | 1 | SMS142 | 30 | 0.246 | 0.002 |
| 24 | 0.9 | 1 | SMS142 | 60 | 2.019 | 0.890 |
| 24 | 1 | 1 | SMS142 | 60 & 70 | 1.850 | 0.618 |
| 24 | 1.1 | 1 | SMS142 | 50 & 60 | 2.742 | 0.436 |
| 24 | 0.3 | 1 | SMS142 | 90 & 105 | 0.282 | 0.037 |
| 24 | 0.5 | 1 | SMS142 | 60 | 0.279 | 0.028 |
| 24 | 0.7 | 1 | SMS142 | 60 | 0.354 | 0.037 |
| 25 | 0.3 | 1 | SMS142 | 30 | NA | NA |
| 25 | 0.5 | 1 | SMS142 | NA | NA | NA |
| 25 | 0.7 | 1 | SMS142 | NA | NA | NA |
| 25 | 0.9 | 1 | SMS142 | NA | NA | NA |
| 25 | 1 | 1 | SMS142 | NA | NA | NA |
| 26 | 0.9 | 1 | SMS142 | 15 | NA | NA |
| 26 | 1 | 1 | SMS142 | 15 | NA | NA |
| 26 | 1.1 | 1 | SMS142 | 15 | NA | NA |
| 26 | 0.3 | 1 | SMS142 | 90 | 4.365 | 2.818 |
| 26 | 0.5 | 1 | SMS142 | 15 | NA | NA |

TABLE 3-continued

Crosslinking Conditions and Results

| Example | SH:Vi molar ratio | Photoinitiator % | Crosslinker | Cure Time (sec) | Adhesion (N/in) | Release (N/in) |
|---|---|---|---|---|---|---|
| 26 | 0.7 | 1 | SMS142 | 15 | NA | NA |
| 26 | 0.7 | 1 | SMS142 | 15 | 3.257 | 2.147 |
| 26 | 0.9 | 1 | SMS142 | 15 | 3.903 | 0.698 |
| 26 | 1 | 1 | SMS142 | 15 | 3.186 | 0.728 |
| 26 | 0.7 | 1 | SMS142 | 15 | 4.115 | 2.335 |
| 26 | 0.9 | 1 | SMS142 | 15 | 3.882 | 0.470 |
| 26 | 1 | 1 | SMS142 | 15 | 3.412 | 0.210 |
| 26 | 0.7 | 1 | SMS142 | 30 | 2.596 | 0.128 |
| 26 | 0.9 | 1 | SMS142 | 30 | 2.097 | 0.063 |
| 26 | 1 | 1 | SMS142 | 30 | 2.024 | 0.046 |
| 26 | 0.9 | 1 | 26298-125 | 60 & 80 | 3.448 | 0.140 |
| 26 | 1 | 1 | 26298-125 | 60 & 85 | 3.3 | 0.162 |
| 26 | 0.3 | 1 | 26298-125 | 80 & 85 | 6.264 | 2.142 |
| 26 | 0.5 | 1 | 26298-125 | 60 & 65 | 4.274 | 0.161 |
| 26 | 0.7 | 1 | 26298-125 | 60 & 65 | 3.463 | 0.041 |
| 27 | NA | 0.5 | 5 wt % Tetraacrylate | 480 | 3.841 | 0.136 |
| 27 | NA | 2 | 5 wt % Tetraacrylate | 90 | 1.574 | 0.024 |
| 27 | NA | 0.5 | 7 wt % Tetraacrylate | 480 | 2.257 | 0.084 |
| 27 | NA | 2 | 7 wt % Tetraacrylate | 60 | 1.561 | 0.034 |
| 28 | 0.3 | 1 | SMS142 | 300 | 0.907 | 0.6 |
| 28 | 0.3 | 1 | SMS142 | 240 | 5.261** | 0.3 |
| 28 | 0.4 | 1 | SMS142 | 150 | 0.569 | 0.439 |
| 28 | 1 | 1 | SMS142 | 240 | 0.982 | 0.1 |

\* Where a ratio is presented, this is a weight ratio of different crosslinkers used in the composition.
\*\*20% cohesive failure was observed for this sample.

INDUSTRIAL APPLICABILITY

The examples show versatility of the skin contact adhesive described herein. Samples with higher adhesiveness (i.e., higher force required to remove) may be useful for certain applications, such as ostomy adhesives and wound dressings that will be left on for longer periods of times, and those with lower adhesiveness (i.e., less force required to remove from the skin) may be useful for applications where the skin contact adhesive will be applied directly to a wound or to a patient with fragile skin. Without wishing to be bound by theory, it is thought that appropriate selection of the polyurethane-polyorganosiloxane copolymer and other ingredients in the crosslinkable composition can be performed to provide skin contact adhesives with appropriate properties for the applications described above.

Example 23 shows that skin contact adhesives can be prepared as described herein including active ingredients without detrimentally affecting said active ingredients when crosslinking the crosslinkable composition used to prepare the skin contact adhesive.

Definitions and Usage of Terms

All amounts, ratios, and percentages are by weight unless otherwise indicated. The articles 'a', 'an', and 'the' each refer to one or more, unless otherwise indicated by the context of specification. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an alkenyl group, an alkynyl group, and an aryl group, an includes the member alkyl individually; the subgroup alkyl and aryl; and any other individual member and subgroup subsumed therein.

"Alkyl" means a saturated monovalent hydrocarbon group. Alkyl is exemplified by, but not limited to, methyl, ethyl, propyl (e.g., iso-propyl and/or n-propyl), butyl (e.g., isobutyl, n-butyl, tert-butyl, and/or sec-butyl), pentyl (e.g., isopentyl, neopentyl, and/or tert-pentyl); hexyl, heptyl, octyl, nonyl, and decyl, as well as branched saturated monovalent hydrocarbon groups of 6 or more carbon atoms.

"Alkenyl" means a monovalent hydrocarbon group containing a double bond. Alkenyl groups are exemplified by, but not limited to, ethenyl, propenyl (e.g., iso-propenyl and/or n-propenyl), butenyl (e.g., isobutenyl, n-butenyl, tert-butenyl, and/or sec-butenyl), pentenyl (e.g., isopentenyl, n-pentenyl, and/or tert-pentenyl), hexenyl, heptenyl, octenyl, nonenyl, and decenyl, as well as such branched groups of 6 or more carbon atoms.

"Alkynyl" means a monovalent hydrocarbon group containing a triple bond. Alkynyl groups are exemplified by, but not limited to, ethynyl, propynyl (e.g., iso-propynyl and/or n-propynyl), butynyl (e.g., isobutynyl, n-butynyl, tert-butynyl, and/or sec-butynyl), pentynyl (e.g., isopentynyl, n-pentynyl, and/or tert-pentynyl), hexynyl, heptynyl, octynyl, nonynyl, and decynyl, as well as such branched groups of 6 or more carbon atoms.

"Aryl" means a cyclic, fully unsaturated, hydrocarbon group. Aryl is exemplified by, but not limited to, cyclopentadienyl, phenyl, anthracenyl, and naphthyl. Monocyclic aryl groups may have 5 to 9 carbon atoms, alternatively 6 to 7 carbon atoms, and alternatively 5 to 6 carbon atoms. Polycyclic aryl groups may have 10 to 18 carbon atoms, alternatively 10 to 14 carbon atoms, and alternatively 12 to 14 carbon atoms.

"Aralkyl" means an alkyl group having a pendant and/or terminal aryl group or an aryl group having a pendant alkyl group. Exemplary aralkyl groups include tolyl, xylyl, benzyl, phenylethyl, phenyl propyl, and phenyl butyl.

"Carbocycle" and "carbocyclic" each mean a hydrocarbon ring. Carbocycles may be monocyclic or alternatively may be fused, bridged, or spiro polycyclic rings. Monocyclic carbocycles may have 3 to 9 carbon atoms, alternatively 4 to 7 carbon atoms, and alternatively 5 to 6 carbon atoms. Polycyclic carbocycles may have 7 to 18 carbon atoms, alternatively 7 to 14 carbon atoms, and alternatively 9 to 10 carbon atoms. Carbocycles may be saturated or partially unsaturated.

"Cycloalkyl" means saturated carbocycle. Monocyclic cycloalkyl groups are exemplified by cyclobutyl, cyclopentyl, and cyclohexyl.

Collectively, the term "monovalent hydrocarbon group" includes alkyl, alkenyl, aryl, aralkyl, and carbocyclic groups, as defined above.

Divalent hydrocarbon group includes alkylene groups such as ethylene, propylene (including isopropylene and n-propylene), and butylene (including n-butylene, t-butylene and isobutylene); and pentylene, hexylene, heptylene, octylene, and branched and linear isomers thereof; arylene groups such as phenylene; and alkaralkylene groups such as:

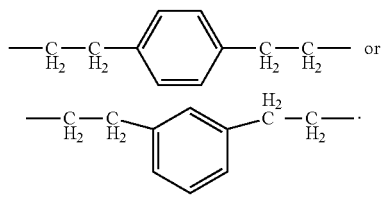

Alternatively, each divalent hydrocarbon group may be ethylene, propylene, butylene or hexylene. Alternatively, each divalent hydrocarbon group may be ethylene or propylene.

"Halogenated hydrocarbon" means a hydrocarbon group as defined above, but where one or more hydrogen atoms bonded to a carbon atom have been formally replaced with a halogen atom. For example, monovalent halogenated hydrocarbon groups can be any one of alkyl, alkenyl, aryl, aralkyl, and carbocyclic groups in which one or more hydrogen atoms bonded to a carbon atom have been replaced with a halogen atom. Monovalent halogenated hydrocarbon groups include haloalkyl groups, halogenated carbocyclic groups, and haloalkenyl groups. Haloalkyl groups include fluorinated alkyl groups such as trifluoromethyl ($CF_3$), fluoromethyl, trifluoroethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4, 3,3-nonafluorohexyl, and 8,8,8,7,7-pentafluorooctyl; and chlorinated alkyl groups such as chloromethyl and 3-chloropropyl. Halogenated carbocyclic groups include fluorinated cycloalkyl groups such as 2,2-difluorocyclopropyl, 2,3-difluorocyclobutyl, 3,4-difluorocyclohexyl, and 3,4-difluoro-5-methylcycloheptyl; and chlorinated cycloalkyl groups such as 2,2-dichlorocyclopropyl, 2,3-dichlorocyclopentyl. Haloalkenyl groups include chloro allyl.

"Transdermal" means being able to pass through unbroken skin. "Skin" includes stratum corneum covered skin and mucosal membranes.

The invention claimed is:

1. A skin contact adhesive composition comprising:
   (A) a polyurethane-polyorganosiloxane copolymer of formula

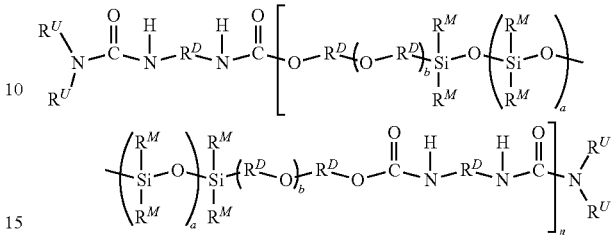

where each $R^U$ is independently a monovalent unsaturated hydrocarbon group; each $R^D$ is independently a divalent hydrocarbon group or a divalent halogenated hydrocarbon group; each $R^M$ is independently a monovalent hydrocarbon group or a monovalent halogenated hydrocarbon group; each subscript b is independently 0 or 1; each subscript a is independently 0 to 100,000; and subscript n is 1 to 10,000;

(B) a curing catalyst,
optionally (C) a crosslinker, and one or both of (D) and (E), where
(D) is an active ingredient, and
(E) is an excipient.

2. The skin contact adhesive composition of claim 1, where in (A) the polyurethane-polyorganosiloxane copolymer
   each $R^U$ is independently an alkenyl group of 2 to 13 carbon atoms; and
   each $R^D$ is independently an alkylene group of 2 to 13 carbon atoms.

3. The skin contact adhesive composition of claim 1, where (C) the crosslinker is present, and the crosslinker is selected from (C1) an acrylate crosslinker, (C2) a crosslinker containing alkenyl groups other than in an acrylate group, (C3) a thiol-functional crosslinker, or (C4) an SiH containing crosslinker.

4. The skin contact adhesive composition of claim 1, where (D) the active ingredient is present, and the active ingredient is selected from drugs that act upon the central nervous system; drugs affecting renal function; drugs affecting cardiovascular function; drugs affecting gastrointestinal function; drugs for treatment of helminthiasis; antimicrobial agents; nutrients; hormones; steroids; and drugs for treatment of dermatoses; non-steroidal anti-inflammatory drugs; propionic acid derivatives; acetic acid derivatives, enolic acid derivatives; anthranilic acid derivatives, COX-2 inhibitors; and local anesthetics.

5. The skin contact adhesive composition of claim 1, where (E) the excipient is present, and the excipient is selected from (F) a stabilizer, (G) a binder, (H) a filler, (I) a solubilizer, (J) a skin penetration enhancer, (K) an adhesion promoter, (L) an agent to improve moisture permeability, or a combination of two or more of (F), (G), (H), (I), (J), (K), and (L).

6. A method comprising:
   1) Mixing ingredients comprising
      (A) a polyurethane-polyorganosiloxane copolymer of formula

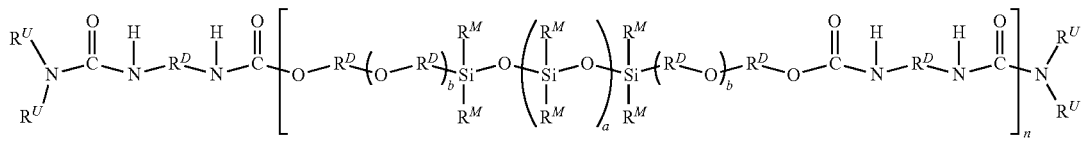

where each $R^U$ is independently a monovalent unsaturated hydrocarbon group; each $R^D$ is independently a divalent hydrocarbon group or a divalent halogenated hydrocarbon group; each $R^M$ is independently a monovalent hydrocarbon group or a monovalent halogenated hydrocarbon group; each subscript b is independently 0 or 1; each subscript a is independently 0 to 100,000; and subscript n is 1 to 10,000, (B) a curing catalyst, optionally (C) a crosslinker, and one or both of (D) and (E), where (D) is an active ingredient, and (E) is an excipient;

thereby preparing a skin contact adhesive composition.

7. The method of claim 6, further comprising:

2) Exposing the crosslinkable composition to heat and/or radiation; thereby preparing a skin contact adhesive.

8. The method of claim 7, where (C) the crosslinker is present, and the crosslinker is selected from (C1) an acrylate crosslinker, (C2) a crosslinker containing alkenyl groups other than in an acrylate group, (C3) a thiol-functional crosslinker, or (C4) an SiH containing crosslinker.

9. The method of claim 7, where (D) the active ingredient is present, and the active ingredient is selected from drugs that act upon the central nervous system; drugs affecting renal function; drugs affecting cardiovascular function; drugs affecting gastrointestinal function; drugs for treatment of helminthiasis; antimicrobial agents; nutrients; hormones; steroids; and drugs for treatment of dermatoses; non-steroidal anti-inflammatory drugs; propionic acid derivatives; acetic acid derivatives, enolic acid derivatives; anthranilic acid derivatives, COX-2 inhibitors; and local anesthetics.

10. The method of claim 7, where (E) the excipient is present, and the excipient is selected from (F) a stabilizer, (G) a binder, (H) a filler, (I) a solubilizer, (J) a skin penetration enhancer, (K) an adhesion promoter, (L) agent to improve moisture permeability, or a combination of two or more of (F), (G), (H), (I), (J), (K), and (L).

11. The method of claim 7, where in (A) the polyurethane-polyorganosiloxane copolymer each $R^U$ is independently an alkenyl group of 2 to 13 carbon atoms; and each $R^D$ is independently an alkylene group of 2 to 13 carbon atoms.

12. A skin contact adhesive prepared by the method of claim 7.

13. A laminate article comprising:

(i) a support having a skin facing surface and an opposed surface, (ii) the skin contact adhesive of claim 12 on at least a portion of the skin facing surface of the support, where the skin contact adhesive has a skin contact surface opposite the skin facing surface of the support, optionally (iii) a release liner covering the skin contact surface of the skin contact adhesive, optionally (iv) an absorbent layer, where the absorbent layer is between the skin facing surface of the support and the skin contact adhesive, or the absorbent layer is mounted to the support so as to contact skin when the laminate article is used; and optionally (v) a carrier mounted to the opposed surface of the support.

14. A coating composition comprising:

(a) a crosslinkable composition comprising (A) a polyurethane-polyorganosiloxane copolymer of formula

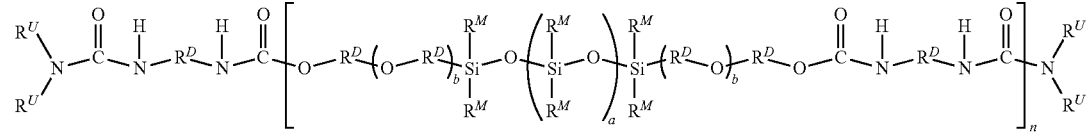

where each $R^U$ is independently a monovalent unsaturated hydrocarbon group; each $R^D$ is independently a divalent hydrocarbon group or a divalent halogenated hydrocarbon group; each $R^M$ is independently a monovalent hydrocarbon group or a monovalent halogenated hydrocarbon group; each subscript b is independently 0 or 1; each subscript a is independently 0 to 100,000; and subscript n is 1 to 10,000, (B) a curing catalyst, and optionally (C) a crosslinker, and (b) a coating additive.

15. The coating composition of claim 14, where in (A) the polyurethane-polyorganosiloxane copolymer each $R^U$ is independently an alkenyl group of 2 to 13 carbon atoms; and each $R^D$ is independently an alkylene group of 2 to 13 carbon atoms.

16. The coating composition of claim 14, where (C) the crosslinker is present, and the crosslinker is selected from (C1) an acrylate crosslinker, (C2) a crosslinker containing alkenyl groups other than in an acrylate group, (C3) a thiol-functional crosslinker, or (C4) an SiH containing crosslinker.

17. The coating composition of claim 14, where (b) the coating additive is selected from (b1) a water scavenger, (b2) a pigment, (b3) a diluent, (b4) a filler, (b5) a rust inhibitor, (b6) a plasticizer, (b7) a thickening agent, (b8) a pigment dispersant, (b9) a flow aid, (b10) a solvent, (b11) an adhesion promoter, (b12) a catalyst, (b13) an organic co-binder, (b14) a siloxane co-binder, (b15) a matting agent, (b16) a leveling agent, (b17) a wax, (b18) a texturizing additive, (b19) an anti-scratching additive, (b20) a gloss modifying additive, (b21) a stabilizer, and (b22) a crosslinker, or a combination of two or more of (b1), (b2), (b3), (b4), (b5), (b6), (b7), (b8), (b9), (b10), (b11), (b12)(b13), (b14), (b15), (b16), (b17), (b18), (b19), (b20), (b21) and (b22).

18. A method comprising:
 i) applying the coating composition of claim 14 to a substrate, and
 ii) crosslinking the coating composition to form a coating.

19. The method of claim 18, where the substrate comprises leather.

* * * * *